United States Patent [19]

Lowe et al.

[11] Patent Number: 5,691,180
[45] Date of Patent: Nov. 25, 1997

[54] DNA SEQUENCE ENCODING N-ACETYL-GALACTOSAMINE-TRANSFERASE

[75] Inventors: John B. Lowe; Peter L. Smith, both of Ann Arbor, Mich.

[73] Assignee: The Regents of the University of Michigan, Ann Arbor, Mich.

[21] Appl. No.: 255,670

[22] Filed: Jun. 9, 1994

[51] Int. Cl.$^6$ .................. C12N 5/00; C07H 21/02; C12Q 1/00; C07K 1/00
[52] U.S. Cl. .................. 435/240.1; 435/4; 435/6; 435/7.1; 435/7.4; 530/350; 536/23.1; 536/23.2; 536/23.4; 935/19; 935/76; 935/77
[58] Field of Search .................. 435/4, 6, 7.1, 7.4, 435/240.1; 536/23.1, 23.2, 23.4; 935/19, 76, 77; 530/350

[56] References Cited

U.S. PATENT DOCUMENTS

| | | | |
|---|---|---|---|
| 4,205,129 | 5/1980 | Podolsky et al. | 435/193 |
| 4,411,994 | 10/1983 | Gilbert et al. | 435/71 |
| 4,438,200 | 3/1984 | Taubman et al. | 435/193 |
| 4,593,004 | 6/1986 | Boross et al. | 435/181 |
| 4,634,665 | 1/1987 | Axel et al. | 435/68 |
| 4,745,055 | 5/1988 | Schenk et al. | 435/7 |
| 5,324,663 | 6/1994 | Lowe | 435/320.1 |

FOREIGN PATENT DOCUMENTS

WO 90/13300  11/1990  WIPO.

OTHER PUBLICATIONS

Lowe et al, FASEB Abstract Form, "Blood Group H α-2-L-Fucosyltransferase Expressed in Mouse Cells After Stable Transfection with Human DNA", (1988).
Kukowska-Latallo et al, (Sep. 22, 1988 Submission to UCLA Glycobiology Symposium).
Ernst et al, (Sep. 22, 1988 Submission to UCLA Glycobiology Symposium).
Lowe et al, (Sep. 22, 1988 Submission to UCLA Glycobiology Symposium).

Ernst et al, *J. Biol. Chem.*, "Stable Expression of Blood Group H Determinants and GDP–L–fucose:β–D–Galactoside 2–α–L–Fucosyltransferase in Mouse Cells after Transfection with Human DNA", (1989) 264, pp. 3436–3447.
Rajan et al, *J. Biol. Chem.*, "A Cloned Human DNA Restriction Fragment Determines Expression of GDP–L–Fucose:β–D–Galactoside 2–α–L–fucosyltransferase in Transfected Cells", (1989) 264, pp. 11158–11167.
Larsen et al, *Proc. Natl. Acad. Sci.*, "Molecular Cloning, Sequence and Expression of a Human GDP–L–fucose:β–D–galactoside 2–α–L–fucosyltransferase cDNA that can Form the H Blood Group Antigen", (1990) 87, pp. 6674–6678.
Larsen et al., *Proc. Natl. Acad. Sci.*, "Isolation of a cDNA Encoding a Murine UDPgalactose:β–D–galactosyl–1, 4–N–acetyl–D–glucosaminide α–1,3–galactosyltransferase: Expression Cloning by Gene Transfer", (1989) 86, pp. 8227–8231.
Graham et al, *Virology*, "A New Technique for the Assay of Infectivity of Human Adenovirus 5 DNA", (1973) 52, pp. 456–467.
Kukowska–Latallo et al, *Genes & Devel.*, "A Cloned Human cDNA determines expression of a Mouse Stage–Specific Embryonic Antigen and the Lewis Blood Group α(1,3/1,4) fucosyltransferase", (1990) 4, pp. 1288–1303.
Weber et al, *Mol. Cell. Biol.*, "Molecular Cloning and Biological Characterization of a Human Gene, ERCC2, That Corrects the Nucleotide Excision Repair Defect in CHO UV5 Cells", (1988) 8, pp. 1137–1146.

(List continued on next page.)

*Primary Examiner*—George C. Elliott
*Assistant Examiner*—Jezia Riley
*Attorney, Agent, or Firm*—Oblon, Spivak, McClelland, Maier & Neustadt, P.C.

[57] ABSTRACT

β1,4-N-acetyl-galactosamine-transferase catalyzes the addition of N-acetyl-galactosamine in β1,4-linkage to subterminal galactose substituted with an α2,3-linked N-acetylneuraminic acid residue.

18 Claims, 11 Drawing Sheets

OTHER PUBLICATIONS

Ripka et al, Biochem. & Biophys. Res. Comm., "DNA–Mediated Transformation of N–Acetylglucosaminyl–transferase I Activity into an Enzyme Deficient Cell Line", (1989), 159, pp. 554–560.

Chao et al, Science, "Gene Transfer and Molecular Cloning of the Human NGF Receptor", (1986), 232, pp. 518–521.

Kavathas et al, Proc. Natl. Acad. Sci., "Stable Transformation of Mouse L Cells for Human Membrane T–Cell Differentiation Antigens, HLA and $\beta_2$–microglobulin: Selection by Fluorescence–activated Cell Sorting", (1983), 80, pp. 524–528.

Southern et al, J. Mol. Appl. Genet., "Transformation of Mammalian Cells to Antibiotic Resistance with a Bacterial Gene Under Control of the SV40 Early Region Promoter", (1982), 1, pp. 327–341.

Kuhn et al, Cell, "Gene Transfer, Expression, and Molecular Cloning of the Human Transferrin Receptor Gene", (1984), 37, pp. 95–103.

Wigler et al, Cell, "Biochemical Transfer of Single–Copy Eucaryotic Genes Using Total Cellular DNA as Donor", (1978), 14, pp. 725–731.

Littman et al, Cell, "The Isolation and Sequence of the Gene Encoding T8: A Molecule Defining Functional Classes of T Lymphocytes", (1985), 40, pp. 237–246.

Toone et al, Tetrahedron, (1989) "Enzyme–Catalyzed Synthesis of Carbohydrates" vol. 45 pp. 5365–5422.

Hodgson, Bio/Techn., "Capitalizing in Carbohydrates", (1990), 8, pp. 83–111 (partial).

Stinson, C&EN, "Controlled Linkage Techniques for Monosaccharides Introduced", (1989), Aug. 28, 1989, pp. 25–26.

C&EN, "Yale Carbohydrate Technology Licensed", (1990), Jan. 15, 1990, pp. 7–8.

Shaper et al, Proc. Natl. Acad. Sci., "Bovine Galactosyltransferase: Identification of a Clone by Direct Immunological Screening of a cDNA Expression Library", (1986), 83, pp. 1573–1577.

Appert et al, Biochem. Biophys. Res. Comm., "Isolation of a cDNA Coding for Human Galactosyltransferase", (1986), 139, pp. 163–168.

Narimatsu et al, Proc. Natl. Acad. Sci., "Cloning and Sequencing of cDNA of Bovine N–acetylglucosamine ($\beta$1–4)galactosyltransferase", (1986), 83, 4720–4724.

Prieels et al, J. Biol. Chem., "Purification of the Lewis Blood Group N–Acetylglucosaminide $\alpha$1–4 Fucosyltransferase and an N–Acetylglucosaminide $\alpha$1–3 Fucosyltransferase from Human Milk", (1981) 256, pp. 10456–10463.

Eppenberger–Castori et al, Glycoconjugate J, "Purification of the N–Acetylglucosaminide $\alpha$(1–3/4) Fucosyltransferase of Human Milk", (1989), 6, pp. 101–114.

Elices et al, J. Biol. Chem., "Purification and Characterization of UDP–Gal"$\beta$–D–Gal(1,4)–D–GlcNAc $\alpha$(1,3)–Galactosyltransferase from Ehrlich Ascites Tumor Cells, (1986) 261, pp. 6064–6072.

Blanken et al, J. Biol. Chem., "Biosynthesis of Terminal Gal$\alpha$1–3Gal$\beta$1–4GlcNAc–R Oligosaccharide Sequences on Glyconconjugates", (1985), 260, pp. 12927–12934.

Beyer et al, J. Biol. Chem., "Purification to Homogeneity of the H Blood Group $\beta$–Galactoside $\alpha$1–2 Fucosyltransferase from Porcine Submaxillary Gland", (1980), 255, pp. 5364–5372.

Beyer et al, J. Biol. Chem., "Enzymatic Properties of the $\beta$–Galactoside $\alpha$1–2 Fucosyltransferase from Porcine Submaxillary Gland", (1980), 255, pp. 5373–5379.

Weinstein et al, J. Biol. Chem., "Primary Structure of $\beta$–Galactoside $\alpha$2,6–Sialyltransferase", (1987), 262, pp. 17735–17743.

Weinstein et al, J. Biol. Chem., "Purification of a Gal$\beta$1–4GlcNAc $\alpha$2–6 Sialyltransferase and a Gal$\beta$1–3(4)GlcNAc $\alpha$2–3 Sialyltransferase to Homogeneity from Rat Liver", (1982), 257, pp. 13835–13844.

Creeger et al, Meth. Enz., "Complex Carbohydrates", (1982), 83, pp. 326–331 (ed. V. Ginsborg).

Natsuka et al, J. Biol. Chem., "Molecular Cloning of a cDNA Encoding a Novel Human Leukocyte $\alpha$–1,3–Fucosyltransferase Capable of Synthesising the Sialyl Lewis x Determinant", (1994), 269(24), pp. 16789–16794.

Natsuka et al, J. Biol. Chem., (Additions and Corrections), "Molecular Cloning of a cDNA Encoding a Novel Human Leukocyte $\alpha$–1,3–Fucosyltransferase Capable of Synthesising the Sialyl Lewis x Determinant", (1994), 269(32), p. 20806.

Sasaki et al, J. Biol. Chem., "Expression Cloning of a Novel $\alpha$–1,3–Fucosyltransferase that is Involved in Biosynthesis of the Sialyl Lewis x Carbohydrate Determinant in Leukocytes", (1994), 269(20), pp. 14730–14737.

Sarnesto et al, J. Biol. Chem., "Purification of the $\beta$–N–Acetylglucosaminide $\alpha$1–3–Fucosyltransferase from Human Serum", (1992), 267, pp. 2745–2752.

Mollicone et al, Eur. J. Biochem., "Acceptor Specificity and Tissue Distribution of Three Human $\alpha$–3–fucosyltransferases", (1990), 191, pp. 169–176.

Holmes et al, J. Biol. Chem., "Biosynthesis of the Sialyl–Le–$^x$ Determinant Carried by Type 2 Chain Glycosphingolipids (IV$^3$NeuAcIII$^3$FucnLe$_4$, VI$^3$NeuAcV$^3$FucnLc$_6$, and VI$^3$NeuAcIII$^3$V$^3$Fuc$_2$nLc$_6$) in Human Lung Carcinoma PC9 Cells", (1986), 261, pp. 3737–3743.

Weston et al, J. Cell. Biochem, "Defining a Glycosyltransferase Gene Family: Cloning and Expression of a Gene Encoding a GDP–Fucose: N–Acetylglucosaminide 3–$\alpha$–L–Fucosyltransferase Homologous to But Distinct from Known Human $\alpha$(1,3)Fucosyltransferases", (1992), p. 150.

Weston et al, J. Biol. Chem., "Isolation of a Novel Human $\alpha$(1,3)Fucosyltransferase Gene and Molecular Comparison to the Human Lewis Blood Group $\alpha$(1,3/1,4)Fucosyltransferase Gene", (1992), 267, pp. 4152–4160.

Holmes et al, J. Biol. Chem., "Enzymatic Basis for the Accumulation of Glycolipids with X and Dimeric X Determinants in Human Lung Cancer Cells (NCI–H69)", (1985), 260, pp. 7619–7627.

Weston et al, J. Biol. Chem., "Molecular Cloning of a Fourth Member of a Human $\alpha$(1,3)Fucosyltransferase Gene Family", (1992), 267, pp. 24575–24584.

Koszdin et al, Biochem. and Biophys. Res. Comm., "The Cloning and Expression of a Human $\alpha$–1,3 Fucosyltransferase Capable of Forming the E–Selectin Ligand", (1992), 187, pp. 152–157.

Nishihara et al, Biochem. and Biophys. Res. Comm., "Human $\alpha$–1,3 Fucosyltransferase (FucT–VI) Gene is Located at Only 13 Kb 3' to the Lewis Type Fucosyltransferase (FucT–III) Gene on Chromosome 19", (1993), 190, pp. 42–46.

Mulligan et al, J. Exp. Med., "Protective Effects of Sialylated Oligosaccharides in Immune Complex–induced Acute Lung Injury", (1993), 178, pp. 623–631.

Mulligan et al, *Nature*, "Protective Effects of Oligosaccharides in P–selectin–dependent Lung Injury", (1993), 364, pp. 149–151.

Dorothy E. Schumm *"Essentials of Biochemistry*, F.A. Davis publishers, Philadelphia, Essentials of Medical Education Series" p. 161 1988.

Geysen et al. "Cognitive features of continuous antigenic determinants" J. Mol. Recognition. 1(1) 32–41 1988.

```
     -41 CT GCG GTA GGC AGT CTG CAG AAG TGG CTG GAG GCT GCG
  1  ATG ACT TCC AGC GTG TCT TTT GCC AGC TTC AGG TTT CCA TGG CTC CTC AAG ACA TTT GTC CTC ATG GTA GGA CTT GCC ACT GTT GCG TTT ATG
  1  Met Thr Ser Ser Val Ser Phe Ala Ser Phe Arg Phe Pro Trp Leu Leu Lys Thr Phe Val Leu Met Val Gly Leu Ala Thr Val Ala Phe Met

94  GTG AGA AAG GTG TCC CTT ACA GAC TTC AGC ACC TTC AAG CCA AAG TTT CCA GAG CCT GCA AGG GTT GAC CCA AAG CTT GAC GTG CTG AAG GTT
 32  Val Arg Lys Val Ser Leu Thr Asp Phe Ser Thr Phe Lys Pro Lys Phe Pro Glu Pro Ala Arg Val Asp Pro Lys Leu Asp Val Leu Lys Val

187  GAG GAG CAT CTG AGG AAA CTC TTT GAC ATC TGG CTC TTC CCC AAA AAT CAG TGT GAC TGT AAC TCT GGC AAA CTG CGA ATG AAA
 63  Glu Glu His Leu Arg Lys Leu Phe Asp Ile Trp Leu Phe Pro Lys Asn Gln Cys Asp Cys Asn Ser Gly Lys Leu Arg Met Lys

280  TAT AAG TTT CAG GAT GCC TAT AAC CAG CTT CCA GCT GTG AGA CAG GCA GAA TTT GAG CAC TTT CAG AGG AGA GAA GGG
 94  Tyr Lys Phe Gln Asp Ala Tyr Asn Gln Leu Pro Ala Val Arg Gln Ala Glu Phe Glu His Phe Gln Arg Arg Glu Gly

373  CTG CCT CGC CCA CCA CCT CTG CTG GCT CCA AAT CTC CCC TTC GGA TAC CCA GTC CAT GGT GTG GAG GTG ATG CCC CTG CAT ACA ATT CTC
125  Leu Pro Arg Pro Pro Pro Leu Leu Ala Pro Asn Leu Pro Phe Gly Tyr Pro Val His Gly Val Glu Val Met Pro Leu His Thr Ile Leu

466  ATC CCA GGC CTC CAG TAT GAA GGG CCA GAT GCT CCA GTC TAT GAG ATC CTG AAA GCT TCT CTG ACA CTG AAC ACC CTT GCT GAT GTG
156  Ile Pro Gly Leu Gln Tyr Glu Gly Pro Asp Ala Pro Val Tyr Glu Ile Leu Lys Ala Ser Leu Thr Leu Asn Thr Leu Ala Asp Val

559  CCA GAT GAT GAG GTT CAG GGC AGA GGC CAG CAG AGG CAG CTG ACC ATT TCC AGA CAT CGG AAG GTC CTG AAT TTC ATC CTT CAG CAT CAG ACG
187  Pro Asp Asp Glu Val Gln Gly Arg Gly Gln Gln Arg Gln Leu Thr Ile Ser Arg His Arg Lys Val Leu Asn Phe Ile Leu Gln His Gln Thr

652  TAC ACC AGC ACA GAG TAC TAT CTC CAC AAG GTG GAC ACA GTA AGT ATG GAA TAC GAG TCG TCA GTG GCC AAG TTT CCA GTG ACT ATC AAA CAA
218  Tyr Thr Ser Thr Glu Tyr Tyr Leu His Lys Val Asp Thr Val Ser Met Glu Tyr Glu Ser Ser Val Ala Lys Phe Pro Val Thr Ile Lys Gln

745  CAG ACT GTA CCC AAG TTG TAT GAC CCT GGA CCT GAG AGG ATC GCC AAG ACT GTG ACC ATT GCC AAG ACT TTT CTC CGT CCC CAC AAG
249  Gln Thr Val Pro Lys Leu Tyr Asp Pro Gly Pro Glu Arg Ile Ala Lys Thr Val Thr Ile Ala Thr Lys Thr Phe Leu Arg Pro His Lys

838  CTT AAG ATC CTG CTT CAG AGT ATT CGA AAA TAT TAC CCA GAC ATT GTA GCT GTA ATT ACC GTG GAT GAC AGC AAG GAG CCC CTG GAA ATT AAT GAT
280  Leu Lys Ile Leu Leu Gln Ser Ile Arg Lys Tyr Tyr Pro Asp Ile Val Ala Val Ile Thr Val Asp Asp Ser Lys Glu Pro Leu Glu Ile Asn Asp
```

FIG. 1A

```
931   GAC TAC GTG GAG TAC TAC ACC ATG CCC TTT GGG AAG GGC TGG TTT GCT GGG AGG AAC CTG GCC ATC TCA CAG GTG ACT ACT AAA TAT GTC CTC
311   Asp Tyr Val Glu Tyr Tyr Thr Met Pro Phe Gly Lys Gly Trp Phe Ala Gly Arg Asn Leu Ala Ile Ser Gln Val Thr Thr Lys Tyr Val Leu

1024  TGG GTG GAC GAT GAC TTT CTC AGC GAC TTC AAG ATT GAG GTA CTG GAT GTC CTG GAG AAA ACC GAA AAG CTG GAG GTG GAT GTG GGC GGC
342   Trp Val Asp Asp Asp Phe Leu Ser Asp Phe Lys Ile Glu Val Leu Asp Val Leu Glu Lys Thr Glu Lys Leu Glu Val Asp Val Gly Gly

1117  AGC GTG CAG GGG AAT ACT TAC CAG CTG AGG TTC TTT CAC GAA CAG AGG TGG GGA TCA TTC CAG GCC
373   Ser Val Gln Gly Asn Thr Tyr Gln Leu Arg Phe Phe His Glu Gln Arg Trp Gly Ser Phe Gln Ala

1210  CTT GAC GGC TTT CCC GGA TGC ACG TTG ACC AGC GTG GTG GTG AAC CAA CTC CGA GAA CAA CTC CGA AGA GTT GGT TTT GAT CCC
404   Leu Asp Gly Phe Pro Gly Cys Thr Leu Thr Ser Val Val Val Asn Phe Leu Ala His Thr Gln Gln Leu Arg Arg Val Gly Phe Asp Pro

1303  ATC TTG CAA CGA GTG GCC CAC GGA GAG TTC TTT ATT GAT GGG CTG GTG GTG TCT TGC CCG GGT GTA ATT ATA AAC CAC CAA
435   Ile Leu Gln Arg Val Ala His Gly Glu Phe Phe Ile Asp Gly Leu Val Val Ser Cys Pro Gly Val Ile Ile Asn His Gln

1396  GTA AGA ACA CCA CCA AAG GAT CCA AAG CTG GCT GCC CTG GCT AAA TAC ACT GAC AAG GAG ATC GTG ATC CAA TTC AAG
466   Val Arg Thr Pro Pro Lys Asp Pro Lys Leu Ala Ala Leu Ala Lys Tyr Thr Asp Lys Glu Ile Val Ile Gln Phe Lys

1489  GTT GCA CTC CAG TAC TTC AAG AAC CAT CTC TAC TGC TCC ACT TAA AAA GTA CCA AGA ATC GCA ATA AAC AGA TTA GCG GCG AAC
497   Val Ala Leu Gln Tyr Phe Lys Asn His Leu Tyr Cys Ser Thr ***

```
CAGGTGACTACTAAATATGTCCTC
  A  A  C  C  G  C  G
  Q  V  T  T  K  Y  V  L
  |  |  |  |  |  |  |  |
  Q  V  T  T  K  Y  V  L

CAGGGGAAT..............ACT
 GC A   TCTCCGGCTTTGCCACC
 Q G N                  T
                        |
 R E I  S G F A         T

GGATGCACGTTGACCAGCGGCGTGGTGAAC
  C  GT G C   GA        T
  G  C  T  L  T  S  G  V  V  N
  |  |     |     |  |  |  |  |
  G  C  V  V  T  D  G  V  V  N

CTGTTGGTGGGCTCTTGCCCGGCTGTA  1421
  TCG   T    C    T C AC  C 1497
  L  L  V  G  S  C  P  G  V
  |  |  |  |  |     |     |
  L  R  V  G  S  C  S  D  V
```

FIG. 5C dna sequence encoding n-acetyl-galactosamine-transferase

BACKGROUND OF THE INVENTION

1. Field of the Invention

The present invention relates to a novel cloned cDNA sequence that encodes a UDP-GalNAc: NeuAcα2,3Galβ-R (1,4) N-acetyl-galactosamine-transferase, its derived protein sequence, other protein and DNA sequences that are derived from the initial cloned sequences, monoclonal antibodies which specifically bind to such enzymes, immunoassays for detecting and/or quantitating such enzymes, plasmids or vectors which contain such a DNA sequence, cells which have been transfected with such a plasmid or vector, and a method of producing such an enzyme by culturing such a transformed cell.

2. Discussion of the Background

CT1 and CT2 are IgM class monoclonal antibodies isolated for their ability to block specific target lysis by a murine cytotoxic T lymphocyte (CTL) clone (Lefrancois, L., et al, *Nature*, Vol. 314, pp. 449–452 (1985); Lefrancois, L., et al, *J. Immunol.*, Vol. 135, pp. 374–383 (1985)). These antibodies recognize overlapping but not identical neoantigenic determinants present on activated cytolytic T-cells, but not on naive populations of T lymphocytes (Lefrancois, L., et al, *Nature*, Vol. 314, pp. 449–452 (1985); Lefrancois, L., et al, *J. Immunol.*, Vol. 135, pp. 374–383 (1985); Lefrancois, L., et al, *J. Exp. Med.*, Vol. 162, pp. 1275–1293 (1985)). Both antibodies strongly stain a variety of independently derived cytotoxic T-lymphocyte cell lines, but do not stain T cell lines of a non-cytolytic phenotype (Lefrancois, L., et al, *Nature*, Vol. 314, pp. 449–452 (1985); Lefrancois, L., et al, *J. Immunol.*, Vol. 135, pp. 374–383 (1985)). Neither antibody recognizes naive T-cell populations in the spleen, thymus, lymph node, or bone marrow (Lefrancois, L., et al, *J. Immunol.*, Vol. 135, pp. 374–383 (1985)). However, both antibodies stain intraepithelial lymphocytes (IEL) (Lefrancois, L., *J. Immunol.*, Vol. 138, pp. 3375–3384 (1987); Goodman, T. G., et al, *J. Immunol.*, Vol. 145, pp. 2959–2966 (1990)), which represent constitutively activated lymphocytes that reside in the intestinal mucosa (Goodman, T., et al, *Nature*, Vol. 333, pp. 855–858 (1988)). Naive splenic T-cells do not express CT reactive determinants, but become CT-positive when induced to generate cytotoxic lymphocytes in mixed lymphocyte cultures (MLC) (Lefrancois, L., et al, *Nature*, Vol. 314, pp. 449–452 (1985); Lefrancois, L., et al, *J. Immunol.*, Vol. 135, pp. 374–383 (1985); Lefrancois, L., et al, *J. Exp. Med.*, Vol. 162, pp. 1275–1293 (1985)). Studies using a T cell hybridoma that can be induced to become cytolytic have shown that the cytokine IL-2 is required for induction of both cytotoxicity and CT antigen expression. Likewise, depletion of IL-2 yields a parallel loss of the cytolytic phenotype and CT antigen expression, confirming a linkage between the activation state of CTL and CT epitope expression (Lefrancois, L., et al, *J. Immunol.*, Vol. 136, pp. 1171–1177 (1986)). The major proteins immunoprecipitated from CTL cell lines by CT antibodies belong to the CD45 family of cell-surface transmembrane tyrosine phosphatases required for T-cell proliferation in response to antigen (Lefrancois, L., et al, *J. Immunol.*, Vol. 135, pp. 374–383 (1985); Pingel, J. T., Cell, Vol. 58, pp. 1055–1065 (1989)).

In parallel studies, it had been shown that murine CTL can also be identified and separated from other lymphocytes by Vicia villosa agglutinin (VVA) (Kimura, A. K., et al,, *J. Exp. Med.*, Vol. 149, pp. 473–484, (1979)), a lectin with nominal specificity for N-acetyl-galactosamine (GalNAc), (Goldstein, I. J., et al, in *The Lectins; Properties, Functions, and Applications in Biology and Medicine*, (Liener, I. E., Sharon, N., and Goldstein, I. J., Eds.) pp. 33–247, Academic Press, Orlando, Fla. (1986)). Through the use of a mutant murine CTL line, Conzelmann and Kornfeld demonstrated that the oligosaccharide structure recognized by VVA was dependent on an enzymatic activity capable of transferring GalNAc in β1,4-linkage to galactose substituted α2,3 with sialic acid, on O- and N-glycosidically linked oligosaccharides (Conzelmann, A., et al, *J. Biol. Chem.*, Vol. 259, pp. 12528–12535 (1984); Conzelmann, A., et al, *J. Biol. Chem.*, Vol. 259, pp. 12536–12542 (1984)). The structure had been defined previously as one commonly known as the $Sd^a$ blood group (Donald, A. S. R., et al, *Biochem. Biophys. Res. Comm.*, Vol. 115, pp. 625–631 (1983)). It was subsequently demonstrated that CT1 and CT2 monoclonal antibodies are capable of binding this epitope, thus defining the CT antibody epitope as, at least in part, the $Sd^a$ blood group oligosaccharide (Conzelmann, A., et al, *J. Exp. Med.*, Vol. 167, pp. 119–131 (1988)).

The structure of the $Sd^a$ blood group was first delineated by Donald et al, as the endo-β-galactosidase released pentasaccharide NeuAcα2,3(GalNAcβ1,4)Galβ1,4GlcNAcβ1,3Gal, on Asn-linked oligosaccharides present on Tamm-Horsefall glycoprotein isolated from human urine (Donald, A. S. R., et al, *Biochem. Biophys. Res. Comm.*, Vol. 115, pp. 625–631 (1983)). This structure is dependent on the addition of β1,4-linked GalNAc to the 3'-sialyl-N-acetyl-lactosamine non-reducing terminus of the oligosaccharide (Serafini-Cessi, F., et al, *Biochem. J.*, Vol. 215, pp. 483–489 (1983); Donald, A. S. R., et al, *Biochem. Soc. trans.*, Vol. 15, pp. 606–608 (1987)). A GalNAc-transferase activity capable of forming this structure has been described in human kidney (Piller, F., et al, *Carbohydrate Res.*, Vol. 149, pp. 171–184 (1986)), intestine (Malagolini, N., et al, *Cancer Res.*, Vol. 49, pp. 6466–6470 (1989)), colon (Morton, J. A., et al, *Immunol. Invest.*, Vol. 17, pp. 217–224 (1988)), urine (Serafini-Cessi, F., et al, *Archives Biochem. Biophys.*, Vol. 266, pp. 573–582 (1988)) and blood plasma (Takeya, A., et al, *J. Biochem.*, Vol. 101, pp. 251–259 (1987)), as well as in guinea pig kidney (Serafini-Cessi, F., et al, *Biochem. J.*, Vol. 215, pp. 483–489 (1983); Dall'olio, F., et al, *Bioscience Reports*, Vol. 7, pp. 925–932 (1987)). These enzyme activities can transfer GalNAc to both N- and O-linked oligosaccharides present on fetuin and hCG, and demonstrate an absolute dependence on galactose substituted α2,3 with sialic acid. Interestingly, these enzyme activities are incapable of efficiently transferring GalNAc to the glycolipid GM3 (NeuAcα2,3Galβ1,4Glc-Cer) despite the fact that they can efficiently use 3'-sialyl-lactose (NeuAcα2,3Galβ1,4Glc) as a substrate (Piller, F., et al, *Carbohydrate Res.*, Vol. 149, pp. 171–184 (1986); Serafini-Cessi, F., et al, *Carbohydrate Res.*, Vol. 151, pp. 65–76 (1986)). Thus, the $Sd^a$ blood, group GalNAc-transferase can transfer GalNAc to the non-reducing terminal 3'-sialyl-lactose and 3'-sialyl-N-acetyl-lactosamine structures of Asn- and Ser/Thr-linked oligosaccharide structures to generate the $Sd^a$ blood group.

However, there remains a need for isolated enzymes which can generate the epitope recognized by the CT, as well as human anti-$Sd^a$ blood group antibodies. There also remains a need for DNA sequences which encode an enzyme which can generate the epitope recognized by the CT, as well as human anti-$Sd^a$ blood group antibodies. There also remains a need for monoclonal antibodies which specifically bind to such an enzyme and immunoassays for detecting and/or quantitating such an enzyme.

SUMMARY OF THE INVENTION

Accordingly, it is an object of the present invention to provide novel DNA sequences which encode an enzyme capable of generating the epitope recognized by CT1 or CT2.

It is another object of the present invention to provide novel DNA sequences which encode an enzymic capable of generating the epitope recognized by human anti-Sd$^a$ blood group antibodies.

It is another object of the present invention to provide plasmids or vectors which contain such a sequence of DNA.

It is another object of the present invention to provide cells transfected with such a plasmid or vector.

It is another object of the present invention to provide novel enzymes which are capable of generating the epitope recognized by the CT1 and CT2.

It is another object of the present invention to provide novel enzymes capable of generating the epitope recognized by human anti-Sd$^a$ blood group antibodies.

It is another object of the present invention to provide novel monoclonal antibodies which specifically bind to such enzymes.

It is another object of the present invention to provide novel immunoassays to detect and/or quantitate such enzymes.

It is another object of the present invention to provide a method for preparing such an enzyme by culturing a cell which has been transformed with such a vector or plasmid.

These and other objects, which will become apparent during the following detailed description, have been achieved by the inventors' cloning and expression of a murine cDNA from a cytotoxic T-lymphocyte cell cDNA library which encodes a UDP-GalNAc: NeuAcα2,3Galβ-Rβ1,4 N-acetyl-galactosamine-transferase capable of generating the epitope recognized by the CT, as well as human anti-Sd$^a$ blood group antibodies.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1A and 1A1 and 1B show the DNA (SEQ. ID NO:1) and derived protein sequence (SEQ. ID NO:2) of the cDNA insert in pCDM8-CT. The predicted amino acid sequence is displayed below the DNA sequence. The putative transmembrane domain (amino acid residues 18–32) is underlined. A schematic representation (FIG. 1B) of the cDNA insert and its predicted protein structure is depicted above the sequences (FIGS. 1A and 1A1). The protein coding region is denoted by a rectangular box. Untranslated sequences are depicted by simple lines. The putative cytosolic, transmembrane (T.M.), and golgi lumen portions of the predicted protein are indicated, and the size of each is listed immediately below in terms of the number of amino acids (a.a.). A single Asn-linked consensus sequence is shown at amino acid residue 389. bp=base pairs (nucleotides);

FIGS. 5A and 5B shows the partial nucleotide and amino acid sequence comparison between the CT-GalNAc-transferase cDNA and a cDNA encoding the human GM2/GD2 synthase (Nagata Y., et al, *J. Biol. Chem.*, pp. 12082–12089 (1992)). The nucleotide and amino acid alignment was generated using the GAP program of the University of Wisconsin Genetics Computer Group (Devereux, et. al. 1984), using a gap weight of 5.0 and a length weight of 0.3. The figure shows only the sequence corresponding to nucleotides 336–1421 of the CT-GalNAc-transferase of the present invention (mCT) (SEQ. ID NO:3) and 373–1497 of the human GM2/GD2 synthase (hGM2) (SEQ. ID NO:5) and their translated amino acid sequences (SEQ. ID NOS:4 and 6, respectively), as these segments correspond to the regions where the two are most homologous. The complete nucleotide sequence of the CT-GalNAc-transferase corresponding to this region is displayed, while only nucleotides that are not identical to the CT-GalNAc-transferase are listed for the human GM2/GD2 synthase. The complete amino acid sequences for this region of both transferases is listed below the nucleotide sequence comparison. Amino acids that are identical between the two sequences are connected by "I". Gaps introduced in the nucleotide sequence and respective amino acid sequence, introduced to maximize alignments, are designated by ".". Two cytidines, missing in the published human GM2/GD2 nucleotide sequence (nucleotides 1296 and 1416 of the human GM2/GD2 sequence; see Examples below and FIGS. 6A and B are designated in bold type;

ID NO:13) is shown on the right, while that of the minus strand is shown on the left. (B) DNA sequence across the region corresponding to nucleotides 1352 to 1361 of the human GM2/GD2 sequence, presented as described in (A); that is, the sequence of the plus strand (SEQ ID NO:14) is shown on the right while the sequence of the minus strand is shown on the left.

DETAILED DESCRIPTION OF THE PREFERRED EMBODIMENTS

Thus, in a first embodiment, the present invention provides novel DNA sequences which encode an enzyme capable of generating the epitope recognized by the CT1 and CT2, as well as human $Sd^a$ blood group antibodies. Suitably, the present DNA sequence is any which encodes the amino acid sequence shown in FIG. 1a. More preferably, the DNA sequence is any which encodes a protein having the sequence corresponding to from position 1 to position 510 in the amino acid sequence shown in FIG. 1a.

Of course, the DNA sequence may encode a protein which corresponds to any of those described above but in which up to 34 amino terminal amino acid residues have been added, deleted, or substituted, provided that the protein retains its activity. In this context a protein is considered to retain its activity if it retains at least 10%, preferably at least ⅓, more preferably at least ½ of the specific activity of the native enzyme to transfer GalNAc to the trisaccharide acceptor 3'-sialyl-N-acetyl-lactosamine as determined by the assay described in the Examples.

In a preferred embodiment, the DNA sequence has the nucleotide sequence shown in FIGS. 1A and 1A1. More preferably, the DNA sequence has the nucleotide sequence corresponding to from position 1 to position 1530 in the nucleotide sequence shown in FIG. 1a.

Figure 1B:
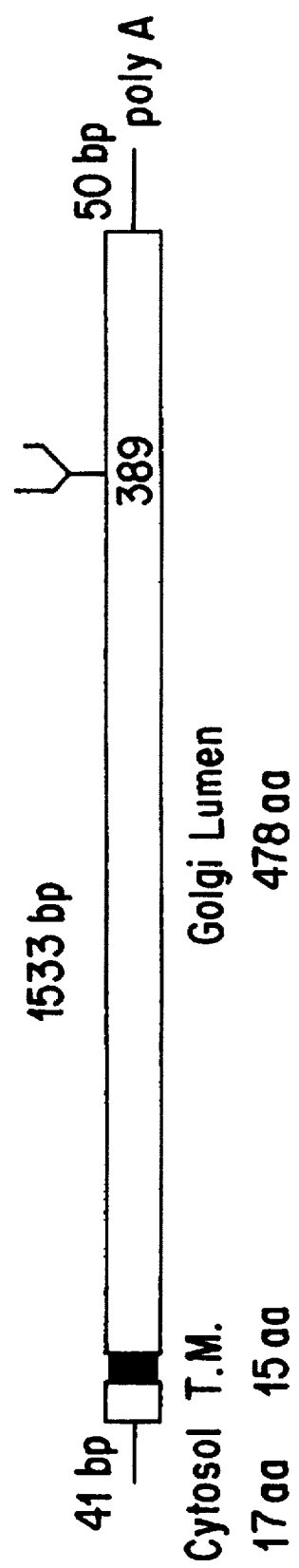

The cloning of the full length DNA sequence shown in FIG. 1b is described in great detail in the Examples below. The shorter length fragments of this sequence as well as the other DNA sequences of the present invention may be obtained by conventional techniques, such as solid state DNA synthesis, site-directed mutagenesis, or the polymerase chain reaction (Maniatis, T., et al, *Molecular Cloning: A Laboratory Manual*, Cold Spring Harbor Laboratory Press, Cold Spring Harbor, N.Y. (1989)).

In another embodiment, the present invention provides novel enzymes capable of generating the epitope recognized by CT1 and CT2, as well as human $Sd^a$ blood group antigens. Suitably, the enzyme has the amino acid sequence shown in FIG. 1b. Alternatively, the enzyme has an amino acid sequence corresponding to from position 35 to position 510 in the amino acid sequence shown in FIG. 1b. As discussed above, the enzyme may also have one of the amino acid sequences described above and in which up to 34 amino terminal amino acid residues have been added, deleted, or substituted.

The present invention also provides novel fusion proteins in which any of the enzymes of the present invention are fused to a polypeptide such as protein A, streptavidin, fragments of c-myc, maltose binding protein, IgG, IgM, amino acid tag, etc. Preferably, the polypeptide fused to the present invention is fused to the amino terminus of the present enzyme. In addition, it is preferred that the polypeptide fused to the enzyme of the present invention is chosen to facilitate the release of the fusion protein from a prokaryotic cell into the culture medium.

In yet another embodiment, the present invention provides novel plasmids or vectors which contain a DNA sequence according to the present invention. The present plasmid may be either a cloning vector or an expression plasmid. Suitable plasmids or vectors are those obtained by inserting a DNA sequence of the present invention into a plasmid or vector such as pCDM8 pCDNA1, pREP8, pCEP4, pTZ18, etc. In the case of an expression plasmid, the DNA sequence of the present invention is preferably inserted into the plasmid downstream from a promoter and in the correct reading frame. The insertion of a DNA sequence according to the present invention into any conventional expression plasmid in the correct reading frame and the insertion of a DNA sequence of the present invention into a conventional cloning vector can easily be accomplished by the skilled artisan using conventional recombinant DNA technology.

The present invention also provides transformed cells which contain a plasmid or vector according to the present invention. Suitable host cells include any mammalian cell. Preferred host cells include Chinese hamster cells, COS cells, etc. The transformation of such host cells with a plasmid or vector according to the present invention may be carried out using conventional techniques (Maniatis, T., et al, *Molecular Cloning: A Laboratory Manual*, Cold Spring Harbor Laboratory Press, Cold Spring Harbor, N.Y. (1989); and Conzelmann, A., et al, *J. Exp. Med.*, vol. 167, pp. 119–131 (1988)).

In another embodiment, the present invention provides a method for producing an enzyme of the present invention by culturing in a culture medium a transformed cell according to the present invention for a time sufficient to produce the enzyme. Preferably, the cell has been transformed with an expression plasmid such as pCDM8-CT. Of course, the particular culture conditions, such as temperature, medium, etc., will depend on the type and identity of the transformed cell. However, the selection of appropriate conditions is well within the abilities of the skilled artisan. For example, suitable culture conditions and media for a variety of cell types are taught in Maniatis, T., et al, *Molecular Cloning: A Laboratory Manual*, Cold Spring Harbor Laboratory Press, Cold Spring Harbor, N.Y. (1989), which is incorporated herein by reference.

In another embodiment, the present invention provides novel monoclonal antibodies which specifically bind to the present enzymes. Such monoclonal antibodies may be produced using conventional methods such as described in Harlow, et al, *Antibodies. A Laboratory Manual*, Cold Spring Harbor Laboratory Press, Cold Spring Harbor, N.Y. (1988), which is incorporated herein by reference. The present antibodies may be labelled with any conventional label, such as a radiolabel, a chromophore (e.g., a fluorescent label), or an enzyme (e.g., horseradish peroxidase).

The present invention also provides novel immunoassays for the detection and/or quantitation of the present enzymes in a sample. The present immunoassays will utilize one or more of the present monoclonal antibodies which specifically bind to the present enzymes. The present immunoassay may be a competitive assay, a sandwich assay, or a displacement assay, such as those described in Harlow, et al, *Antibodies. A Laboratory Manual*, Cold Spring Harbor Laboratory Press, Cold Spring Harbor, N.Y. (1988) and Ausebel, F. M., et al, *Current Protocols in Molecular Biology*, John Wiley and Sons, NY (1989) and may rely on the signal generated by a radiolabel, a chromophore, or an enzyme.

The DNA sequences, enzymes, plasmids, cells, and methods of the present invention have a number of uses. Thus, the present invention provides a previously undiscovered DNA sequence that encodes a specific and a heretofore undiscovered protein sequence capable of functioning as a UDP-GalNAc: NeuAcα2,3Galβ-Rβ(1,4) N-acetyl-galactosamine-transferase. This enzyme, when expressed by the cloned DNA sequence described here, has been shown to function within mammalian cells to generate de novo expression of specific cell surface glycoconjugate structures on those cells. These structures are recognized by antibodies that recognize the terminal oligosaccharide epitope NeuAcα2,3(GalNacβ1,4)Galβ-R. This enzyme, when expressed by the cloned DNA sequence described here, has also been shown to function in the enzymatic manner implied in its name, when assayed in extracts prepared from cells that express the DNA sequence. The oligosaccharide products of this enzyme represents N-acetyl-galactosamine linked in beta 1,4 configuration to the galactose residue of a "type II" 3'-sialyl-N-acetyl-lactosamine acceptor (hereinafter referred to as sub-terminal B(1,4) GalNAc residues). This reaction is shown in the equation below:

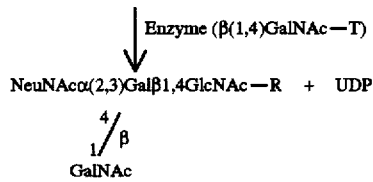

The product may also be written as

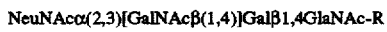

wherein R is a N-linked or O-linked oligosaccharide moiety or backbone.

Specific utilities of the various embodiments of the present invention include:

i. Construction of animal cell lines with specific capabilities with respect to post-translational modification of the oligosaccharides on cell-surface, intracellular, or secreted proteins or lipids with sub-terminal β(1,4) GalNAc residues that represent the products of this enzyme (for the production of diagnostics and therapeutics by the biotechnology industry). Specifically, the cloned DNA sequence described here can be introduced by conventional techniques into a mammalian cell line that does not normally express the cognate enzyme or its product (sub-terminal β(1,4) GalNAc residues on oligosaccharides), and transcribed in that cell in the "sense" direction, to yield a cell line capable of expressing sub-terminal β(1,4) GalNAc residues on oligosaccharides on cell-surface, intracellular, or secreted proteins or lipids.

Alternatively, this cloned DNA sequence can be introduced by conventional techniques into a mammalian cell line that does express the cognate enzyme and its product (subterminal β(1,4) GalNAc residues) and transcribed in that cell in the "antisense" direction, to yield a cell line incapable of expressing sub-terminal β(1,4) GalNAc residues on cell-surface, intracellular, or secreted proteins or lipids. The introduction and "antisense" expression of the present DNA sequences may be carried out as described in Maniatis, T., et al, *Molecular Cloning: A Laboratory Manual*, Cold Spring Harbor Laboratory Press, Cold Spring Harbor, N.Y. (1989). The endogenous UDP-GalNAc: NeuAcα2,3Galβ-R β(1,4) N-acetyl-galactosamine-transferase gene(s), in a mammalian cell expressing the cognate enzyme(s), can be inactivated with the DNA sequence described here by homologous recombination techniques, or by "anti-sense" oligonucleotide approaches based upon the DNA sequence described herein, or by dominant negative mutant N-acetyl-galactosaminyltransferase sequences that inactivate endogenous UDP-GalNAc: NeuAcα2,3Galβ-R β(1,4) N-acetyl-galactosamine-transferase(s) and that may be derived via mutagenesis and genetic selection techniques.

In this way, it is possible to construct animal cell lines that are suitable host cells for the production of diagnostic or therapeutic materials whose usefulness or efficacy depends upon the specific post-translational modification determined by this cloned DNA sequence and its cognate enzyme. For example, it is known that the biological effectiveness of many therapeutic proteins or peptides, recombinant or otherwise, can depend critically upon the oligosaccharide structure(s) that are covalently attached to them. The structure of these oligosaccharides is primarily a function of the number and kind of glycosyltransferase enzymes that are found in the cell used to produce these therapeutic products. Animal cells and yeasts are competent to perform these glycosylation reactions; however, not all glycosyltransferase enzymes are produced by every animal cell or yeast, and therefore, some oligosaccharide structures (including sub-terminal β1,4-GalNAc residues generated by the present enzymes encoded by the present DNA sequences) are not produced by them.

The converse is also true, namely, that producing cells may express a glycosyltransferase analogous to, or identical to, the present UDP-GalNAc: NeuAcα2,3Galβ-R β(1,4) N-acetyl-galactosaminetransferase encoded by the present DNA sequences. The presence of Sub-terminal β(1,4) GalNAc residues alters the bioactivity of natural or recombinant therapeutic or diagnostic agents (glycoproteins or glycolipids) produced by mammalian or other eukaryotic hosts. Eukaryotic host cells used to produce these recombinant agents can be altered to add sub-terminal β1,4-GalNAc residues to the oligosaccharides on a recombinant product by expressing all or part of the present DNA sequences described here in the desired host. Alternatively, sub-terminal β(1,4) GalNAc residues may be eliminated from the product produced in these host cells by the use of transfected "anti-sense" vector constructs, recombination-based gene inactivation, "anti-sense" oligonucleotide approaches, or dominant negative mutant fucosyltransferases, outlined above.

Conventional methods for obtaining a product having a particular oligosaccharide residue include an empirical approach to identify a cell line that does or does not express a particular enzyme or an enzyme that functions in a similar or identical manner, for the production of the appropriately modified recombinant or natural product. This is not always optimal since cell lines with a particular post-translation modification capability may not exist naturally, or may not be especially suited to high level production of an appropriately modified product. Unwanted sub-terminal β(1,4) GalNAc residues present on a therapeutic material produced by an empirically identified animal cell line must be removed chemically or enzymatically, a process that may be costly or inefficient.

The advantages of using the present DNA sequence in conjunction with the techniques outlined above, relative to these older methods, include the ability to construct lines that specifically lack the capability to generate sub-terminal β(1,4) GalNAc residues on the oligosaccharides of glycoproteins (and possibly glycolipids). Properly constructed, these cell lines will eliminate any need for chemical or enzymatic treatment of a therapeutic or diagnostic material to remove unwanted sub-terminal β(1,4) GalNAc residues. Moreover, when sub-terminal β(1,4) GalNAc residues are desirable for a particular diagnostic or therapeutic product produced by animal cells, cell lines may be engineered with the cloned DNA sequence described here to generate these residues.

ii. Isolation of reagents suitable for efficient enzymatic synthesis and production of oligosaccharides (in enzyme reactors, for example).

Oligosaccharides may be used as immunomodulatory reagents in the field of organ transplantation. In particular, soluble and solid-phase oligosaccharides may block or ameliorate antibody-mediated organ transplant rejection in cases involving incompatibility due to differences in the major blood group antigen systems of the organ donor and the recipient, including the Sd$^a$ blood group system (the oligosaccharide structure generated by the UDP-GalNAc: NeuAcα2,3Galβ-R β(1,4) N-acetyl-galactosamine-transferase enzyme is identical to the human Sd$^a$ blood group antigen).

Likewise, soluble oligosaccharides may be used as therapeutic agents that function by blocking attachment of bacterial, viral, or parasitic pathogens to glycoconjugate "receptors" found on the surface of the animal tissues that these pathogens invade. For example, the precursor oligosaccharide structure, which serves as a substrate for the UDP-GalNAc: NeuAcα2,3Galβ-R β(1,4) N-acetyl-galactosamine-transferase, (namely 3' sialyl-N-acetyl-lactosamine on Asn- and Ser/Thr-linked oligosaccharides) also serves as a "receptor" for some forms of uropathogenic bacteria. This interaction may be inhibited by modification of this structure by the addition of sub-terminal β(1,4) GalNAc residues.

Moreover, glycoconjugates, including sub-terminal β(1,4) GalNAc residues modulate adhesive events between cells, and between cells and their environment during developmental and differentiation processes. These events include homing of pro-thymocytes to the thymus or involvement in modulating ontological events of prothymocytes within the thymus. In addition, the sub-terminal β(1,4) GalNAc residues have been shown to be largely associated with the CD45 family of T-cell surface tyrosine-phosphatases. This family is required for the proliferation of T-cells in response to foreign antigen stimulation. Furthermore, in chimeric protein experiments involving these molecules it has been shown that the catalytic activity of this molecule is constitutively functional unless the extra-cellular domains of adjacent molecules are cross-linked together, in which case the catalytic activity of the CD45 molecule is down regulated and the T-cell is no longer able to proliferate in response to antigen stimulation. The proliferative ability of T-lymphocytes may be controlled by effecting the down regulation of CD45 by the addition of sub-terminal β(1,4) GalNAc residues to oligosaccharides on CD45 isoforms which result in the interaction with specific receptor molecules. Alternatively, addition of such sub-terminal β(1,4) GalNAc residues to oligosaccharides on CD45 isoforms will block recognition of the CD45 molecules by otherwise down-modulating counter-receptors, and thus operate to maintain constitutively expressed CD45 activity. Thus, the present GalNAc-transferase sequence may be used to construct oligosaccharide-type molecules, capable of disrupting, maintaining, or otherwise modulating the function of normal, or perhaps even malignant, T-lymphocytes.

Currently, oligosaccharides are produced by chemical synthesis (a procedure that is inefficient and costly) or by isolation from natural sources (using costly and inefficient procedures that often require the processing of large quantities of animal or plant material, and the purification of the desired oligosaccharide from other contaminating oligosaccharides). The present invention provides a mechanism to synthesize abundant quantities of purified UDP-GalNAc: NeuAcα2,3Galβ-R β(1,4) N-acetyl-galactosamine-transferase, which may be used to construct an enzyme bioreactor (enzyme in solution or immobilized on a solid phase matrix, for example via the protein-A moiety fused to the catalytic domain of the enzyme, as described in the Examples capable of enzymatic synthesis of structures containing sub-terminal β(1,4) GalNAc residues.

The use of the present enzyme is more efficient than approaches involving chemical synthesis of structures containing sub-terminal β(1,4) GalNAc residues or their purification from natural sources, for a variety of reasons. One, the only chemicals necessary would be the enzyme substrates; these are easily obtained or synthesized. Two, enzymatic synthesis of such structures produce only the desired product and the nucleotide diphosphate product of substrate hydrolysis. This latter chemical is found as the natural byproducts of these reactions in animal cells, is relatively non-toxic, and is easily separated from the oligosaccharide synthetic product. By contrast, chemical synthetic procedures typically generate numerous products of side reactions which must be removed, and which may be toxic as well. Similarly, purification of oligosaccharides from natural sources requires the removal of other contaminating oligosaccharides present in the natural material. Three, enzymatic catalysis is extraordinarily efficient; nearly complete conversion of substrate to product may be achieved. By contrast, chemical synthesis of sub-terminal β(1,4) GalNAc residues on oligosaccharides is a multi-step process; yields at each step may be much less than 100%, and the cumulative efficiency of current chemical synthesis procedures does not approach the efficiency possible with enzymatic synthesis.

Similarly, purification of oligosaccharides with sub-terminal β(1,4) GalNAc residues from natural materials can entail significant losses inherent to the purification procedures required to separate the desired oligosaccharide from contaminating, irrelevant oligosaccharides, with inefficient isolation of the desired oligosaccharide. Although the UDP-GalNAc: NeuAcα2,3Galβ-R β(1,4) N-acetyl-galactosamine-transferase encoded by the present DNA sequences may be partially purified from animal tissues for synthetic use, these purifications are themselves inefficient, primarily because the enzyme is typically present in very low abundance.

The present invention provides two methods for the abundant production of this enzyme. First, this may be done through the construction and selection of animal cells that produce relatively large quantities of the enzymes. Alternatively, the present DNA sequences may be used with conventional recombinant DNA technologies to produce large quantities of the present glycosyltransferases in yeasts or in prokaryotic hosts. Furthermore, the present DNA sequence may be modified via standard molecular cloning schemes or mutagenesis to yield a recombinant fucosyltransferase with novel properties that make it more desirable than the wild-type enzyme. For example, the modifications might be made to the enzyme that make it more stable, or more suitable for immobilization in a bioreactor.

iii. Isolation of reagents suitable for producing recombinant UDP-GalNAc: NeuAcα2,3Galβ-R β(1,4) N-acetyl-galactosamine-transferase to be used directly as a research reagent, or to be used to generate antibodies against the UDP-GalNAc: NeuAcα2,3Galβ-R β(1,4) N-acetyl-galactosamine-transferase, for research applications.

The present invention provides two methods for producing large quantities of this enzyme (see ii. above—i.e. specially constructed animal cells, or via natural or synthetic genes encoding these enzymes) which may be used as a research tool with which to study the structures and functions of oligosaccharides and glycoproteins. Likewise, the enzyme produced by this method, or the nucleic acid sequence and derived protein sequence provided by this method, may be used to generate antibodies to this enzyme (via synthetic peptides). These antibodies might also be used as research reagents to study the biosynthesis and processing of these enzymes, and might be used as an aid in their purification for all the uses described in this disclosure.

iv. Recombinant enzyme for use in screening natural and synthetic compounds for fucosyltransferase inhibitors or inactivators.

There may be an association between the numbers of cell surface sub-terminal β(1,4) GalNAc residues on oligosaccharides of a cell and the ability of that cell to metastasize in a malignant fashion. If there is a causal relationship here, drugs that inhibit the present enzyme may be used as antitumor agents. The present enzyme may be used for screening compounds for anti-GalNAc transferase activity, since the cloned sequence may be used with standard techniques to produce relatively large amounts of pure GalNAc transferase. This will aid in screening, since the effects of potential inhibitors will be tested on a pure enzyme, without the confounding effects that may occur in whole cell extracts or with partially purified enzyme.

v. Engineering of glycosyltransferase substrate specificity to generate novel glycoconjugate structures on secreted or cell-associated glycoconjugates.

The present cloned UDP-GalNAc: NeuAcα2,3Galβ-R β(1,4) N-acetyl-galactosamine-transferase cDNA may be used to generate mutant UDP-GalNAc: NeuAcα2,3Galβ-R β(1,4) N-acetyl-galactosamine-transferases that generate glycosidic linkages different from that generated by the wild-type enzyme. These novel linkages may or may not be naturally occurring, and may enhance bioactivity of the molecules to which they are attached. Alternatively, mutagenesis and selection approaches may be used to generate mutant UDP-GalNAc: NeuAcα2,3Galβ-R β(1,4) N-acetyl-galactosamine-transferase that act in a dominant negative fashion. The dominant negative mutants so generated might be used to inactivate endogenous glycosyltransferase activities when the product(s) of such an enzyme are not desired. Mutant UDP-GalNAc: NeuAcα2,3Galβ-R β(1, 4) N-acetyl-galactosamine-transferase might also be generated, for example, that function as N-acetyl-galactosminyltransferases that hydrolyze various sugar linkages (GalNAc, Gal, GlucNAc, fucose, mannose, or others) from oligosaccharides in vitro and in vivo.

vi. Genotyping individuals at this GalNAc transferase locus.

Absence of a GalNAc-transferase similar or identical to the one encoded by the cDNA sequence detailed here has been found in several families. Restriction fragment length polymorphisms within or linked to the gene corresponding to this cloned gene segment may be used to genotype individuals at this locus, for the purpose of genetic counseling. Likewise, the molecular basis for any detrimental phenotypes might be elucidated via the study of the gene segment described here, should it be causally-related to such phenotypes.

The present invention will now be described in more detail in the context of the cloning of the full length cDNA fragment shown in FIG. 1a. However, it should be understood that this description is not limiting.

The monoclonal antibodies CT1 and CT2 were originally selected by virtue of their ability to block the cytolytic activity of a murine CTL cell line (Lefrancois, L., et al, Nature, Vol. 314, pp. 449–452 (1985)). These antibodies react with several T-lymphocyte cell lines with a cytotoxic phenotype, but not with helper T-lymphocytes (Lefrancois, L., et al, Nature, Vol. 314, pp. 449–452 (1985); Lefrancois, L., et al, J. Immunol., Vol. 135, pp. 374–383 (1985); Lefrancois, L., et al, J. Exp. Med., Vol. 162, pp. 1275–1293 (1985)). Characterization of the epitope(s) recognized by these antibodies indicate that they can recognize, as a minimal structure, specific oligosaccacharide molecules displayed by Asn- and Ser/Thr-linked oligosaccharides (NeuAcα2,3(GalNAcβ1,4)Galβ1,4-R) (Conzelmann, A., et al, J. Exp. Med., Vol. 167, pp. 119–131 (1988)). However, the epitopes recognized by the CT1 and CT2 antibodies are not identical, in that the CT1 antibody can block CT2 binding, but not vice versa (Lefrancois, L., et al, J. Immunol., Vol. 135, pp. 374–383 (1985)), suggesting the possible involvement of additional determinants beyond this trisaccharide structure. Other biochemical analyses indicate that the bulk of these epitopes are displayed at the surface of CTL by various isoforms of the CD45 (T200) molecule (Lefrancois, L., et al, J. Immunol., Vol. 135, pp. 374–383 (1985)), a transmembrane glycoprotein whose cytosolic domain maintains tyrosine phosphatase activity required for antigen-dependent T-lymphocyte proliferation (Pingel, J. T., Cell, Vol. 58, pp. 1055–1065 (1989)).

The present inventors have now isolated a cloned cDNA corresponding to the regulated UDP-GalNAc: NeuAcα2, 3Galβ1,4-R β1,4-N-acetyl-galactosamine-transferase activity that catalyzes the enzymatic conversion of constitutively expressed precursor oligosaccharides to the CT epitope(s). Sequence analysis of the cDNA indicates that it encodes a 58 kDa protein with a predicted type II membrane topology characteristic of glycosyltransferases. Gene fusion experiments confirm that this cDNA encodes β1,4-N-acetyl-galactosamine-transferase activity that constructs epitopes recognized by the CT antibodies.

Sequence analysis of the enzyme indicates that it shares a substantial amount of protein sequence similarity with the human GM2/GD2 synthase (Nagata Y., et al, J. Biol. Chem., pp. 12082–12089 (1992)). This is perhaps not surprising since GM2/GD2 synthase also transfers GalNAc from the nucleotide sugar donor UDP-GalNAc to oligosaccharide precursors terminating in NeuAcα2,3Gaβ1,4-R moieties. Additional glycolipid structures have been described that possess a terminal trisaccharide motif [NeuAcα2,3 (GalNAcβ1,4)Galβ1,4] virtually identical to the $Sd^a$ structure or GM2. These structures include GalNAc-GM1b (Itoh, T., et al, J. Biol. Chem., Vol. 256, pp. 165–169 (1981)), GalNAc-GD1a (Svennerholm, L., et al, *J. Biol. Chem.*, Vol. 248, pp. 740–742 (1973)), and GalNAc-sialylparagloboside (Gillard, B. K., et al, *Biochemistry*, Vol. 27, pp. 4601–4606 (1988)). As noted above, the CT1 and CT2 antibodies can recognize an oligosaccharide structure that is identical to the human Sd$^a$ blood group determinant.

Other features of the invention will become apparent in the course of the following descriptions of exemplary embodiments which are given for illustrations of the invention and are not intended to be limiting thereof.

EXAMPLES

Methods

Cell lines.

The murine cytotoxic T-lymphocyte cell line, 14-7fd (Braciale, T. J., et al, *J. Exp. Med.*, Vol. 153, pp. 910–923 (1981); Andrew, M. E., et al, *J. Immunol*, Vol. 132, pp. 839–844 (1984)) was obtained from Dr. Vivian Braciale (University of Virginia) and was propagated in Iscove's (Gibco) containing 10% heat-inactivated fetal bovine serum (Hyclone), 5% mouse concanavalin A supernatant (Braciale, T. J., et al, *J. Exp. Med.*, Vol. 153, pp. 910–923 (1981)), and antibiotics. CHO-Tag cells were constructed by co-transfecting CHO Ade-C cells with 20 µg of Bam HI linearized pSVE-Bla (Muller, W. J., et al, *Mol. Cell. Biol.*, Vol. 4, pp. 2406–2412 (1984)), containing the polyoma T-antigens, and Eco-RI linearized pSV2-Neo (Southern, P. J., et al, *J. Mol. Appl. Genet.*, Vol. 1, pp. 327–341 (1982)) in a 10:1 ratio, using a calcium phosphate procedure (Chen, C., et al, *Mol. Cell. Biol.*, Vol. 7, pp. 2745–2752 (1987)). After selection for G-418 resistant colonies, cells containing the polyoma large T-antigen were identified by immunofluorescence using an anti-polyoma large T-antigen murine monoclonal antibody (Oncogene Sciences, Seattle) (Dilworth, S. M., et al, *Proc. Natl. Acad. Sci. U.S.A.*, Vol. 79, pp. 1059–1063 (1982)). Individual clones were further characterized for their ability to replicate exogenously introduced plasmid DNA by transfecting them (see below) with pCDM8-chloramphenicol acetyl-transferase (pCDM8-CAT), and subjecting them to Southern blotting after restriction enzyme digestion with Dpn I or Mbo I (Hefferman, M., et al, *Nucleic Acids Res.*, Vol. 19, pp. 85–92 (1991)). Plasmids replicating within CHO-Tag cells are resistant to restriction with Dpn I and sensitive to Mbo I, whereas, bacterially replicated plasmid shows the opposite pattern of sensitivity to these two enzymes. CAT enzyme expression was determined in parallel using extracts prepared from the transfectants and a phase separation method with butyryl—Coenzyme A and $^3$H-Chloramphenicol as the substrates (Seed, B., et al, *Gene*, Vol. 67, pp. 271–277 (1988)). CHO-Tag cells were propagated in α-MEM (supplemented with deoxyribonucleotides and ribonucleotides; Gibco) containing 10% heat inactivated fetal bovine serum, 0.4 mg/ml G-418 (active drug; Gibco), penicillin, and streptomycin.

cDNA library construction.

An oligo-dT primed cDNA library was prepared from poly(A)$^+$ RNA isolated from 14-7fd cells, as previously described (Aruffo, A., et al, *Proc. Natl. Acad. Sci. U.S.A.*, Vol. 94, pp. 8573–8577 (1987)), except the cDNA was ligated into the mammalian expression vector pCDM8 (Seed, B., *Nature*, Vol. 329, pp. 840–842 (1987)). The library contained 1.5×10$^7$ independent recombinants with a mean insert size of approximately 1 kb.

Transfection of CHO-Tag cells.

CHO-Tag cells were tranfected using a commercially available transfection reagent (DOTAP, Boehringer-Mannheim), and either CsCl banded DNA (Maniatis, T., et al, *Molecular Cloning: A Laboratory Manual*, Cold Spring Harbor, N.Y. (1982)), or "mini-prep" DNA prepared using a commercially available kit (Magic Millipreps, Promega). Cells were plated 24 hours prior to transfection, at a density of 1×10$^6$ cells per 100 mm plate. 2 µg of plasmid DNA was mixed with 2 mls of serum-free α-MEM, and in a separate tube, 72 ml of DOTAP was mixed with 2 ml of serum-free α-MEM. The two solutions were subsequently combined, and incubated for 20 minutes at room temperature. The DNA/DOTAP/α-MEM solution was then added to cell monolayers that had been washed once with serum-free α-MEM, and the cells were returned to the incubator. Three hours later, 8 ml of serum-replete α-MEM was added. This media was removed 24 hours later, and was replaced with 10 ml of complete media. This procedure yielded a 30–35% transfection efficiency as assessed by flow cytometry of cells transfected with a cDNA encoding an α(1,3/1,4)-fucosyltransferase (pCDM8-FTIII) (Kukowska-Latallo, J. F., et al, *Genes & Dev.*, Vol. 4, pp. 1288–1303 (1990)) and stained with the antibody CSLEX (Fukushima, K., et al, *Cancer Res.*, Vol. 44, pp. 5279–5285 (1984)). This same insert in the vector pCDM7 (Aruffo, A., et al, *Proc. Natl. Acad. Sci. U.S.A.*, Vol. 94, pp. 8573–8577 (1987)), which does not contain the polyoma origin of replication, but does have the SV-40 origin of replication, yields a transfection efficiency of 11% after staining with the CSLEX antibody.

Preparation of panning dishes.

Bacterial petri dishes (60 mm, Falcon 1007) were coated with 4 ml of second antibody solution (10 mg/ml goat anti-mouse IgM, Sigma; in 50 mM Tris-HCl, pH 9.5) overnight at 4° C. Plates were then washed with PBS, pH 7.3, containing 1 mM EDTA, and were subsequently blocked for 1 hour at room temperature with 1 mg/ml BSA in PBS. Plates were washed again with PBS/EDTA, and were coated with primary antibody by incubating with 0.5 ml of CT2 antibody (ascites) diluted 1:50 in staining media (DMEM, 2% fetal bovine serum, 10 mM HEPES, pH 7.5, and 0.1% sodium azide) for 30 minutes at 4° C. Remaining unbound primary antibody was then removed by washing the dishes with staining media.

cDNA library screening.

Forty 100 mm plates were transfected with plasmid DNA prepared from an amplified portion of the library. After a 68 hour expression period, the cells were detached from the plate using 3 mM EDTA in PBS. After washing the cells with staining media, the resulting cell pellets were each resuspended in 2 ml of staining media and applied to a panning dish (~2×10$^7$ cells/dish). The cells were allowed to settle onto the panning dishes, and were allowed to incubate there for 1 hour at 4° C. Non adherent cells were then removed by washing the plates 4 times with 4 ml of PBS/1 mM EDTA. Plasmid DNA was rescued from the adherent cells using the Hirt supernatant method (Hirt, B., *Mol. Biol.*, Vol. 26, pp. 365–369 (1967)), and introduced by electrotransformation into the *E. coli* host MC1061/P3 (Seed, B., et al, *Proc. Natl. Acad. Sci. U.S.A.*, Vol. 87, pp. 3365–3369 (1987)). Plasmid DNA was prepared from these transformants and was subjected to two additional rounds of screening by the same procedure, except that only 10 plates were transfected on the third round. Panning-directed "sib" selection (Larsen, R. D., et al, *Proc. Natl. Acad. Sci. U.S.A.*, Vol. 86, pp. 8227–8231 (1989)), starting from a pool of 500 bacterial colonies, was employed to isolate a single bacterial clone harboring a plasmid capable of directing transfected CHO-Tag cells to adhere to CT2 coated panning dishes.

Northern and Southern blotting 14-7fd cell poly (A)⁺ RNA was subjected to Northern blot analysis using blotting and hybridization conditions described previously (Larsen, R. D., et al, *Proc. Natl. Acad. Sci. U.S.A.*, Vol. 86, pp. 827–8231 (1989)). The probe consisted of the 1.6 kb Xho I insert isolated from pCDM8-CT, labeled (Feinberg, A. P. et al, *Anal. Biochem.*, Vol. 132, pp. 6–13 (1983)) with [α-$^{32}$P]dCTP to a specific activity of 1×10$^9$ cpm/mg. The blot was subjected to three 10 minute washes in room temperature 2× SSC, and a 30 minute wash in 2× SSC, 0.2% SDS at 55° C., and was then subjected to autoradiography.

Murine genomic DNA was prepared and subjected to restriction digestion as described previously (Ernst, L. K., et al, *J. Biol. Chem.*, Vol. 264, pp. 3436–3447 (1989)). Genomic DNA restriction digests were fractionated by electrophoresis through 1.2% agarose gels, in a manner that yielded duplicate sets of fractionated digests, and the fractionated digests were transferred to Hybond-N (Amersham). The blot was then divided into two halves in such a manner that each contained identical sets of samples. One blot was probed with a Bsm I-Ear I fragment corresponding to nucleotides 523–1040 of the murine Sd$^a$ insert. The other was probed with a fragment corresponding to nucleotides 580–1144 of the human GM2/GD2 synthase cDNA (Nagata Y., et al, *J. Biol. Chem.*, pp. 12082–12089 (1992)) isolated from a human melanoma (M21) cDNA library with the polymerase chain reaction (see below). These probes correspond to regions where these two sequences maintain optimal nucleotide sequence alignment. Both probes were labeled (Feinberg, A. P. et al, *Anal. Biochem.*, Vol. 132, pp. 6–13 (1983)) with [α-$^{32}$P]dCTP to a specific activity of 2.3×10$^9$ cpm/mg. Blots were hybridized at 32° C. for 16 hours in a hybridization solution described previously (Ernst, L. K., et al, *J. Biol. Chem.*, Vol. 264, pp. 3436–3447 (1989)), were washed three times for 10 minutes in 2× SSC at room temperature, and were then washed for 30 minutes at 50° C. in 2× SSC, 0.2% SDS. The blots were exposed to XAR5 for seven days, were subjected to an additional wash for 30 minutes at 65° C. in 0.1× SSC, 0.5% SDS, and were again processed for autoradiography.

Flow cytometry analysis.

Transfected CHO-Tag cells were harvested after a 68 hour expression period, and were stained as previously described. Primary murine monoclonal IgM antibodies were diluted in the following concentrations: Anti-blood group H antibodies (Chembiomed Ltd., Edmonton, Alberta; 10 mg/ml), CT1 and CT2 (generously provided by Dr. Leo Lefrancois; 1:50 dilution of ascites) (Lefrancois, L., et al, *J. Immunol.*, Vol. 135, pp. 374–383 (1985), 2A3D2 and 2D11E2 (generously provided by Dr. Reiji Kannagi; 1:100 dilution of purified ascites) (Hiraiwa, N., et al, *Cancer Res.*, Vol. 50, pp. 5497–5503 (1990)). Cells were then stained with a fluorescein-conjugated goat anti-mouse IgM (Sigma; 40 mg/ml). Human anti-serum from Sd$^a$ blood group deficient individuals (Donald, A. S. R., et al, *Biochem. Soc, trans.*, Vol. 15, pp. 606–608 (1987)) was generously provided by Dr. Winifred Watkins and was used at a dilution of 1:50. Cells stained with these latter serum were processed for flow cytometry using a mixture of fluorescein-conjugated goat anti-human IgG and fluorescein-conjugated goat antihuman IgM (Sigma; 40 mg/ml each). Vicia villosa (VVA) was used as a direct fluorescein-conjugate (EY labs; 2 mg/ml). All stained cells were subjected to analysis by flow cytometry on a FACScan (Bectin-Dickenson) as previously described (Kukowska-Latallo, et al, *Genes & Dev.*, Vol. 4, pp. 1288–1303 (1990)).

DNA sequence analysis.

DNA sequencing was done with the dideoxy chain termination method (Sanger, F., et al, *Proc. Natl. Acad. Sci. U.S.A.*, Vol. 74, pp. 5463–5467 (1977)) using a commercially available kit (USB) and synthetic oligonucleotide primers. DNA and protein sequence analysis was performed using the sequence analysis software package of the University of Wisconsin Genetics Computer Group (Devereux, J., et al, *Nucleic Acids Res.*, Vol. 12, pp. 387–395 (1984)) and the MacVector version of the IBI Pustell Sequence Analysis Software package (IBI).

N-Acetyl-galactosamine-transferase assays.

Cultured cells or tissues were used to isolate crude microsomes. Tissues were disrupted with a polytron, and cultured cells were disrupted with a sonicator, in buffer C (30 mM Tris, pH=7.5, 120 mM potassium chloride, 5 mM magnesium acetate, 0.02% sodium azide) containing 0.25M sucrose. The homogenates were subjected to centrifugation at 1000×g for 20 minutes. The resulting supernatants were layered onto a cushion of 1.3M sucrose in Buffer C, and centrifuged for 3 hours at 120,000×g. Microsomes were collected from the 0.25M sucrose/1.3M sucrose interface, were diluted 5-fold with buffer C, and were pelleted. The resulting pellets were resuspended in 0.5 mls of 10 mM HEPES, pH 7.5, 20% glycerol, and were stored at −80° C.

GalNAc-transferase assays were performed in 25 mM HEPES (pH 7.5), 20 mM MnCl$_2$, 3 mM ATP, 10% glycerol, 85 mM GlcNAc, 0.03% Triton X-100, 20 mM UDP-[$^3$H]GalNAc (250,000 cpm), containing 88 µg of either iminobiotinylated (Orr, G. A., *J. Biol. Chem.*, Vol. 256, pp. 761–766 (1981)) fetuin (~4 nmoles terminal 3' sialic acid) or iminobiotinylated asialo fetuin, in a total volume of 50 ml. Assays were incubated for 90 minutes at 37° C. and were terminated by the addition of 950 ml of wash buffer (50 mM NH$_4$CO$_3$, pH=10.25, 0.5M NaCl). Each terminated assay was then centrifuged 5 minutes to remove precipitate, and was then applied to a 3 ml column of avidin-agarose (Pierce) that had been pre-equilibrated with 15 mls of wash buffer. The column was subjected to three 5 ml washes and was then eluted with 3 ml of elution buffer (50 mM ammonium acetate, pH 4.0, 0.5M NaCl). The eluate was mixed with 3 ml of water, and 36 ml of BioSafe II (RPI), and was subjected to scintillation counting. Fetuin and asialo fetuin (Sigma) were iminobiotinylated by resuspending them in 1 ml of 0.1M NaHCO$_3$ at 10 mg/ml, adding 0.1 ml of 8 mg/ml NHS-iminobiotin (Pierce) dissolved in DMSO, and incubating overnight at 4° C. The iminobiotinylated material was then dialyzed against two 1 liter changes deionized water, and was stored at −20° C. until use.

Assays using low molecular oligosaccharides as substrates (3'-sialyl-N-acetyl-lactosamine, and lactosamine) were conducted exactly as described above, using 4 nmole of respective substrate, except that assays were terminated by adding 950 ml 5 mM NaH$_2$PO$_4$ (pH 6.8). After a brief centrifugation, the supernatant was applied to a 3 ml column of Dowex 1X-8 (PO$_4$; Biorad) that had been preequilibrated in 5 mM NaH$_2$PO$_4$ (pH 6.8) (Paulson, J. C., et al, *J. Biol. Chem.*, Vol. 252, pp. 2363–2371 (1977)). The column was eluted with 2 mls of the same buffer. All three mls were collected, mixed with 18 mls of BioSafe II, and subjected to scintillation counting.

Enzyme assay product analysis.

Enzyme product used for structural confirmation was prepared using 3'-sialyl-N-acetyl-lactosamine as the substrate, and assays conditions described above, except that the radiolabeled product in the Dowex column eluate was dried under vacuum, and desalted over P-2 in deionized H$_2$O. Aliquots (5000 cpms) were subjected to desialylation by hydrolysis in 2N acetic acid in a boiling water bath for varying lengths of time. The samples were then dried under vacuum. Residual acetic acid was eliminated from the samples by repeatedly resuspending them in water, and redrying them under vacuum. The product was then resuspended in water and subjected to ion-exchange HPLC on an AX-5 column as described (Baenziger, J. U., et al, *Anal. Biochem.*, Vol. 112, pp. 357-361 (1981)), except that a 12 minute isocratic phase was incorporated prior to the commencement of the KPO$_4$ [?] gradient. Desialylated material eluted at 5 minutes, and monosialylated material eluted at 13 minutes. For preparative isolation of desialylated assay product, 50,000 cpms was subjected to acid hydrolysis for 45 minutes The material was then repeatedly dried under vacuum and resuspended in water, as described above, and a fraction was subjected to digestion with jack bean β-hexosaminidase (Oxford Glycosystems) in 50 mM sodium citrate, pH 4.4, 0.02% sodium azide, for 96 hours at 37° C. 0.3 units of the enzyme were added at the beginning of the digestion, and 0.15 additional units were added after 24 and 48 hours Release of [$^3$H]GalNAc from the desialylated product was determined on an Aminex HPX-87H organic acid analysis HPLC column (Biorad) operated isocratically in 0.01N sulfuric acid (Green, E. D., et al, *J. Biol. Chem.*, Vol. 260, pp. 5623-5630 (1985)). Undigested [$^3$H] tetrasaccharide product eluted at 8 minutes, while 2N acetic acid-treated material eluted at 11 minutes, and [$^3$H]GalNAc eluted at 15 minutes.

PCR amplification of human GM2/GD2 synthase fragments.

Two distinct regions of the human GM2/GD2 synthase cDNA were prepared by the PCR, using a cDNA library constructed with mRNA isolated from a human melanoma cell line (M21) (Mueller, B. M., et al, *Proc. Natl. Acad. Sci. U.S.A.*, Vol. 87, pp. 5702-5705 (1990)). Primers were designed based on the published sequence for the human GM2/GD2 synthase (Nagata Y., et al, *J. Biol. Chem.*, pp. 12082-12089 (1992)). The first region corresponds to nucleotides 520-1084 (upper strand primer (SEQ. ID NO:7): gcgcctcGAGGTATACCAGGTGAACCTGACTGCCTCC, corresponding to nucleotides 520-550, extraneous nucleotides in lower case, synthetic Xho I site underlined; lower strand primer (SEQ. ID NO:8): gcgctcgagTGAAGACGAAGTCGTCGTCCACCC, corresponding to the reverse complement of nucleotides 1061-1084, synthetic Xho I site underlined). The second region corresponds to nucleotides 1181-1692 (upper strand primer (SEQ. ID NO:9): gcgctcgagCCACTTATCGGCAGCTGCTGAGCGTGGAGC, corresponding to nucleotides 1181-1210, synthetic Xho I site underlined; lower strand primer (SEQ. ID NO:10): gcgcctcGAGTGCTCACAGGGTGGTGGGGTTTGTTGG, corresponding to the reverse complement of nucleotides 1663-1692, synthetic Xho I site underlined). PCR reactions contained 0.5 μg of template DNA, 2.5 ng of each primer, 10 mM Tris-HCl, 50 mM KCl, 3 mM MgCl$_2$, 10 mM DTT, 4 mM of each deoxynucleotide, and 0.5 units of Taq polymerase (Perkin-Elmer-Cetus). Thirty cycles of amplification were performed, consisting of 1.5 minutes at 94° C., followed by an annealing step for 1 minute at 65° C., and an extension for 1.5 minutes at 72° C. The PCR product corresponding to nucleotides 520-1084 was digested with Xho I, gel purified, and cloned into the Xho I site of pCDM8. A representative plasmid was amplified and sequenced to confirm its identity. The product corresponding to nucleotides 1181-1692 was isolated in an identical manner, except that the fragment was independently generated three times. A cloned representative of each was sequenced. The three maintained identical sequences, indicating that each was free of any PCR-dependent mutation.

Construction and analysis of pPROTA-CT$_c$.

A 1441-bp segment of the cDNA insert containing the putative GalNAc-transferase catalytic domain was isolated from pCDM8-CT by the PCR. PCR conditions were exactly as described above, except that 50 ng of pCDM8-CT plasmid DNA was used as the template, and the reactions were only cycled for 15 rounds, in order to prevent introduction of PCR-dependent sequence changes. PCR primers were chosen to amplify a segment corresponding to the enzyme's putative catalytic domain, and to allow the fragment to be cloned into the EcoRI site of the vector pPROTA (Sanchez-Lopez, R., et al, *J. Biol. Chem.*, Vol. 263, pp. 11892-11899 (1988)) so as to yield a fusion protein consisting of the protein A segment of pPROTA, fused, in frame, to the coding region of the enzyme's catalytic domain. These primers correspond to nucleotides 100-129 (upper strand (SEQ. ID NO:11): cgcgaattcGGTGTCCCTTACAACA-GACTTCAGCACC; extraneous nucleotides in lower case, synthetic Eco RI site underlined) and to nucleotides 1512-1541 (lower strand primer (SEQ. ID NO:12): cgcgaattcGGTACTTTTTAAGTGGAGCAGTAGAGATGG, reverse complement). The PCR product was digested with Eco RI, gel purified, and ligated into the Eco RI site of pPROTA. A representative plasmid containing a single insert in the appropriate orientation was designated pPROTA-CT$_c$.

The plasmids pPROTA-CT$_c$ (pPROTA contains an SV-40 origin of replication and has a replication efficiency similar to that noted above for pCDM7 vectors) and pCDM8-CT were transfected into two 100 mm plates each of CHO-Tag cells as described above. After a 68 hour expression period, the medium (20 mls of each) was harvested, and clarified by centrifugation at 1000×g for 20 minutes to remove any residual cells. One aliquot of each supernatant was directly assayed for GalNAc-transferase activity. The remainder of each supernatant was used in IgG-Sepharose binding studies. IgG-Sepharose, or Sepharose 4B (0.5 ml packed volume each; Pharmacia) were pre-equilibrated by washing twice with 1 ml of TBS, 1 mg/ml BSA, 0.5% Triton X-100, and twice with 1 ml of TBS, 1 mg/ml BSA, in a batchwise manner. One half of each clarified supernatant was incubated overnight at 4° C. with the equilibrated IgG-Sepharose or Sepharose 4B matrix. The matrices were then pelleted (400×g, 2'min) through 0.5 ml of 1M sucrose in TBS. The supernatant was removed and an aliquot was subjected to GalNAc-transferase assay ("unbound" fraction). The matrices were washed twice with 1 ml of TBS/BSA/Triton X-100, and then twice with 1 ml of TBS/BSA. The matrices were resuspended in an equal volume of TBS/BSA, and assayed directly for GalNAc-transferase activity ("bound" fraction). The adherent cells were harvested using 3 mM EDTA in PBS and pelleted. The cells were resuspended in 10 mM HEPES, 20% glycerol, were sonicated, and were centrifuged at 1000×g for 20 minutes to generate a post nuclear supernatant which was also assayed for GalNAc-transferase activity ("cell-associated" fraction).

Results

Expression Cloning Approach.

In order to isolate a cDNA encoding an enzyme capable of generating the oligosaccharide structure recognized by the CT antibodies, a gene transfer approach first developed for cloning cDNAs that encode cell surface proteins (Aruffo, A., et al, *Proc. Natl. Acad. Sci. U.S.A.*, Vol. 94, pp.

8573–8577 (1987); Seed, B., et al, *Proc. Natl. Acad. Sci. U.S.A.*, Vol. 87, pp. 3365–3369 (1987)), and adapted by us for the isolation of glycosyltransferase cDNA's (Kukowska-Latallo, et al, *Genes & Dev.*, Vol. 4, pp. 1288–1303 (1990); Larsen, R. D., et al, *Proc. Natl. Acad. Sci. U.S.A.*, Vol. 86, pp. 827–8231 (1989) was employed. This approach involves transfection of a mammalian cDNA expression library into a CT antigen-deficient cultured mammalian host cell capable of constructing the CT antigen upon introduction of a CT-GalNAc-transferase activity, followed by the rescue of cDNAs that determine expression of this cell surface oligosaccharide antigen.

The present GalNAc-transferase catalyzes the transfer of GalNAc from the donor nucleotide sugar substrate UDP-GalNAc to oligosaccharide substrates that terminate with 3-O-N-acetyl-neuraminic acid substituted galactose (i.e., 3'-sialyl-N-acetyl-lactosamine). Therefore, a suitable host cell line must synthesize both of these substrates, but must be devoid of any endogenous CT-GalNAc-transferase activity. In addition it must be capable of expressing exogenously introduced episomal DNA (containing CT-GalNAc-transferase-determining cDNAs) at sufficiently high levels to allow detection of the enzyme's cell surface oligosaccharide product. Chinese hamster ovary (CHO) cells fulfilled these requirements. CHO cells express Asn-and Ser/Thr-linked oligosaccharides that terminate almost exclusively with 3'-sialyl-N-acetyl-lactosamine (Smith, P. L., et al, *J. Biol. Chem.*, Vol. 265, pp. 874–881 (1990)), and that represent the precursor oligosaccharide substrate of the CT-GalNActransferase (Conzelmann, A., et al, *J. Biol. Chem.*, Vol. 259, pp. 12528–12535 (1984); Conzelmann, A., et al, *J. Biol. Chem.*, Vol. 259, pp. 12536–12542 (1984); Conzelmann, A., et al, *J. Exp. Med.*, Vol. 167, pp. 119–131 (1988); Conzelmann, A., et al, *Biochem. J.*, Vol. 242, pp. 817–824 (1987)). Furthermore, they do not express any endogenous CT-GalNAc-transferase as assessed by in vitro enzymatic assay, nor do they express detectable levels of CT (or $Sd^a$) antibody reactive material on their cell surface. It is known that CHO cells also synthesize UDP-GalNAc, as evidenced by the presence of Ser- and Thr-linked oligosaccharides, whose synthesis is dependent on UDP-GalNAc (Kingsley, D. M., et al, Cell, Vol. 44, pp. 749–759 (1986)). To insure high level expression of transfected expression cDNA libraries in the CHO host cells, we stably transfected our parental CHO cell line with a plasmid vector that encodes the polyoma large T-antigen (Hefferman, M., et al, *Nucleic Acids Res.*, Vol. 19, pp. 85–92 (1991)). The resulting host cells (CHO-Tag) allow high level, episomal replication of expression vectors bearing the polyoma origin of replication (e.g. pCDM8) (Seed, B., *Nature*, Vol. 329, pp. 840–842 (1987)), and facilitate high expression levels of molecules encoded by such vectors, as well as rescue of such vectors by the Hirt supernatant procedure (Hirt, B., *Mol. Biol.*, Vol. 26, pp. 365–369 (1967)).

Isolation of a cloned cDNA that determines expression of the CT2 epitope.

A murine CTL line, 14-7fd, has been shown to express large amounts of CT-GalNAc-transferase activity in an in vitro assay (Conzelmann, A., et al, *Biochem. J.*, Vol. 242, pp. 817–824 (1987)). These results were confirmed using fetuin and the trisaccharide 3'-Sialyl-N-acetyl-lactosamine as substrates for transfer, using microsomes prepared from this cell line. This CTL line is also strongly reactive with both CT antibodies, as well as with human anti-$Sd^a$ serum, when analyzed by flow cytometry procedures. This cell line was therefore used as a source of mRNA for constructing a cDNA expression library in the expression vector pCDM8.

Plasmid DNA amplified from the 14-7fd cell library was transfected into CHO-Tag cells and the transfected cells were panned on petri dishes coated with the CT2 antibody. Plasmid DNA was rescued from adherent cells with the Hirt supernatant method (Hirt, B., *Mol. Biol.*, Vol. 26, pp. 365–369 (1967)), was transformed into bacteria and amplified. This amplified plasmid DNA was transfected into CHO-Tag cells, and the transfected cells were again panned on petri dishes coated with the CT2 antibody. Plasmid DNA was rescued from adherent cells, transformed into bacteria, amplified, and subjected to a third round of transfection and selection by panning. Bacterial clones obtained with plasmid DNA rescued from this third round of panning were divided into several pools of clones comprised of between 50 to 2000 independent colonies. Plasmid DNA was prepared from each pool, and was separately transfected into CHO-Tag cells. The transfected cells were then tested for their ability to adhere to plates coated with the CT2 antibody. The plasmid DNA isolated from one 500 colony pool yielded CT2-adherent CHO-Tag cells after transfection. This pool was divided into several smaller pools, and plasmid DNAs prepared from these pools were separately tested for their ability to determine CT2-adherent phenotype in transfected CHO-Tag cells. This process was repeated until we identified a single plasmid clone, PCDM8-CT, that yielded a CT2-adherent phenotype when transfected into CHO-Tag cells.

The cDNA insert in pCDM8-CT predicts a type II transmembrane glycosyltransferase.

The cDNA insert in pCDM8-CT is 1624 nucleotides in length. It contains a single long open reading frame of 1533 bp that begins at a position compatible with the Kozak consensus sequence for translational initiation (FIGS. 1A and 1A1 and 1B) (Kozak, M., Cell, Vol. 44, pp. 283–292 (1986)). This assignment predicts a 41 bp 5'-untranslated region and a 50 base pair long 3'-untranslated region (FIG. 1). The open reading frame predicts a 510 amino acid protein with a calculated molecular weight of 58,313 daltons. Inspection and hydropathy analysis (Kyte, J., et al, *J. Mol. Biol.*, Vol. 157, pp. 105–132 (1982)) of this polypeptide sequence predicts a type II transmembrane protein (Wickner, W. T., et al, *Science*, Vol. 230, pp. 400–407 (1985)) with a short (17 amino acid) cytosolic domain at its amino terminus, a 15 amino acid transmembrane domain flanked by basic residues, and a 478 amino acid carboxyl-terminal domain. The sequence organization and membrane-spanning topology predicted for this protein are virtually identical to those predicted by the sequences of all mammalian glycosyltransferases cloned to date (Paulson, J. C., et al, *J. Biol Chem.*, Vol. 264, pp. 17615–17618 (1989)). These considerations strongly suggest that the protein encoded by pCDM8-CT is a glycosyltransferase. They further indicate that the 478 residues at the carboxyl-terminus of the enzyme reside within the lumen of the Golgi apparatus and constitute the protein's catalytic domain.

Figure 2:
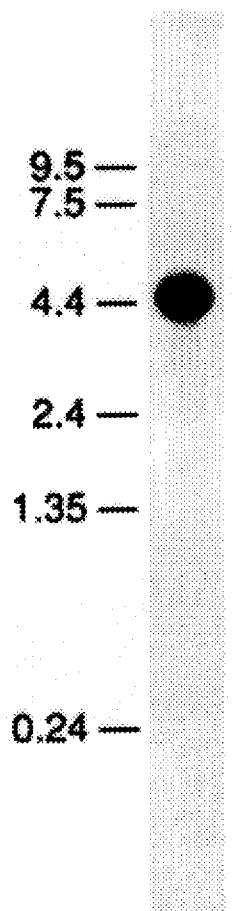
FIG. 2 shows the results of a Northern blot analysis of 14-7fd cells. 2 μg of oligo-dT purified RNA isolated from 14-7fd cells was subjected to Northern blot analysis. The blot was probed with a radiolabeled Xho-I fragment representing the entire 1.6 kb insert in pCDM8-CT. RNA molecular size standards are indicated on the left (in kilobases)

This cloned cDNA hybridizes to a prominent 4.4 kb transcript in 14-7fd cells (FIG. 2). This indicates that cDNA we have isolated does not represent a full length transcript. Nonetheless, we believe we have isolated the entire coding region of this enzyme since this cDNA insert is capable of expressing an enzyme with functional catalytic activity corresponding to the murine CT-GalNAc-transferase (see below). The discrepancy between the transcript size and the cDNA can most probably be accounted for by an incomplete representation of the 5' and 3' untranslated regions, especially when considered with the fact that many mammalian glycosyltransferase transcripts contain extremely long 3' untranslated regions (Lowe, J. B., *Sem. Cell Biol.*, Vol. 2, pp. 289–307 (1991)). However, this does not rule out the possibility that a less abundant smaller transcript from the 14-7fd library, which is not readily evident upon Northern blot analysis, has been cloned.

The protein encoded by pCDM8-CT is a UDP-GalNAc: NeuAcα2,3Galβ-R β1,4-GalNAc-transferase.

Figure 3:
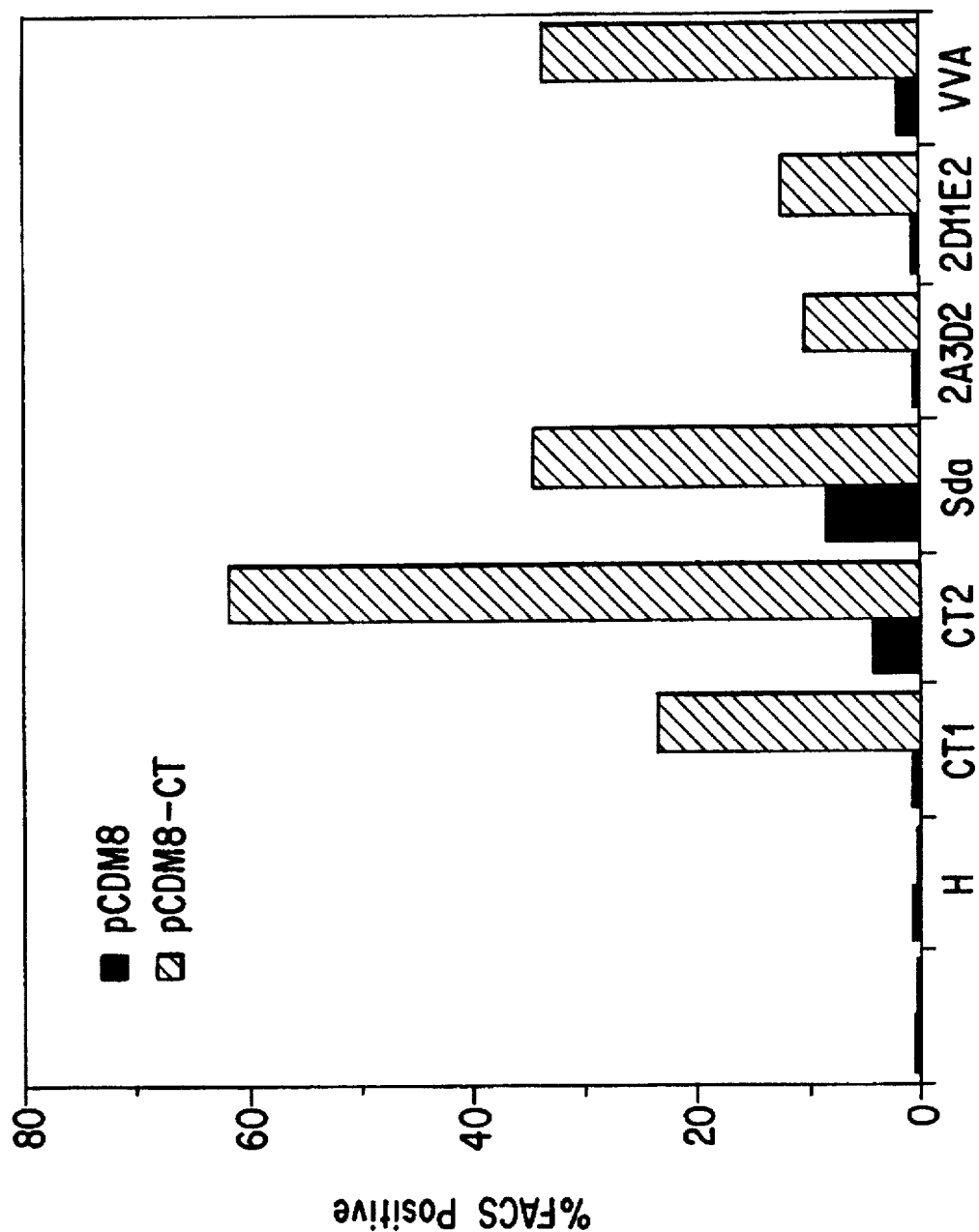
FIG. 3 illustrates the results of the flow cytometry analysis of pCDM8-CT transfected CHO-Tag cells. CHO-Tag cells were transfected with either the expression vector pCDM8-CT (hashed bars) or the control vector (pCDM8; solid bars) alone. After a 68 hour expression period, cells were harvested and subjected to flow cytometry analysis with the monoclonal antibodies or lectin indicated, using methods detailed in the Examples below. The data represent the percentage of cells staining more intensely than an arbitrary limit determined from cells stained with FITC conjugated goat anti-mouse IgM alone.

Flow cytometry analysis and enzyme assays were used to confirm that pCDM8-CT encodes a GalNAc-transferase capable of transferring GalNAc in a β1,4-linkage to galactose in the presence of an α2,3-linked sialic acid. In the flow cytometry studies, plasmid pCDM8-CT, or a negative control vector (pCDM8), were transiently transfected into CHO-Tag cells, and the transfected cells were subsequently examined using antibodies and a lectin that recognize the NeuAcα2,3(GalNAcβ1,4)Galβ-R structure (FIG. 3). CHO-Tag cells transfected with pCDM8-CT express epitopes recognized by the CT1 and CT2 monoclonal antibodies (FIG. 3), and also stain with a human alloantiserum that recognizes the human $Sd^a$ blood group determinant (Donald, A. S. R., et al, *Biochem. Soc, trans.*, Vol. 15, pp. 606–608 (1987)) (FIG. 3). The transfected cells also stain brightly with two monoclonal antibodies (2A3D2 and 2D11E2) (Hiraiwa, N., et al, *Cancer Res.*, Vol. 50, pp. 5497–5503 (1990)) shown previously to recognize the $Sd^a$ blood group on Ser/Thr-linked oligosaccharides, as well as the non-reducing terminal trisaccharide structure NeuAc α2,3 (GalNAcβ1,4)Gal-R of glycolipids such as GM2 and GalNAc-GD1a (Hiraiwa, N., et al, *Cancer Res.*, Vol. 50, pp. 5497–5503 (1990)). These cells also stained brightly with fluorescein isothiocyanate-conjugated Vicia villosa agglutinin (VVA), a GalNAc specific lectin that binds to wild type murine cytotoxic T-lymphocytes (Kimura, A. K., et al., *J. Exp. Med.*, Vol. 149, pp. 473–484 (1979). By contrast, a negative control IgM antibody directed against the human H blood group did not stain cells transfected with pCDM8-CT, nor did it stain cells transfected with the vector alone. These results demonstrate that the cDNA we have isolated is competent to construct the cell surface localized terminal carbohydrate structure NeuAcα2,3(GalNAcβ1,4)Gal-R.

Figure 4:
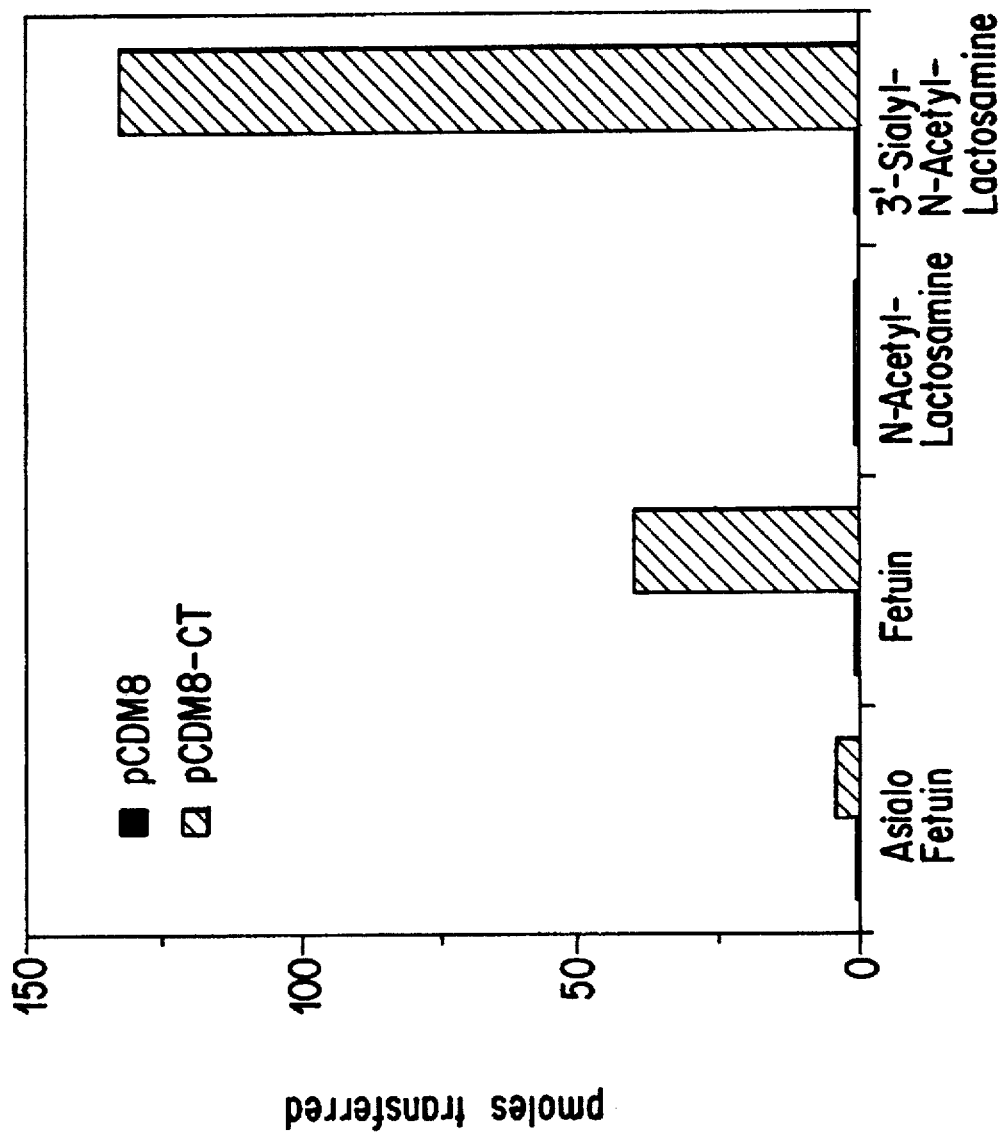
FIG. 4 shows the results of β1,4-N-acetyl-galactosamine-transferase assays of pCDM8-CT transfected CHO-Tag cells. CHO-Tag cells were transfected with either pCDM8-CT or pCDM8 alone. After a 68 hour expression period, crude microsomal fractions were isolated and assayed for β1,4-N-acetyl-galactosamine-transferase activity as described in the Examples below. Assays using microsomes prepared from pCDM8-CT and pCDM8 transfected CHO-Tag cells are shown as hatched bars and solid bars, respectively. All acceptors were present at a concentration of 80 μM 3'-sialyl-N-acetyl-lactosamine or N-acetyl-lactosamine (for iminobiotinylated fetuin and asialo-fetuin this was an estimate based on data presented by Green et. al.) (Green, E. D., et al, *J. Biol. Chem.*, Vol. 263, pp. 18253–18268 (1988)). The donor nucleotide sugar was present at a concentration of 20 μM (1 nmole)

Enzyme assays were used to obtain additional confirmatory evidence for this conclusion. These assays were conducted using microsomes isolated from CHO-Tag cells transiently transfected with pCDM8-CT, or from CHO-Tag cells transiently transfected with the vector pCDM8 alone. Microsomal fractions were tested for their ability to transfer GalNAc from the nucleotide donor sugar UDP-GalNAc to various acceptor substrates. As documented in FIG. 4, microsomes prepared from pCDM8-CT transfected cells were proficient at transferring GalNAc to the trisaccharide acceptor 3'-sialyl-N-acetyl-lactosamine, and generated the tetrasaccharide structure NeuAcα2,3(GalNAcβ1,4)Galβ1, 4GlcNAc (see below). However, this microsomal fraction did not utilize the unsialylated disaccharide N-acetyl-lactosamine at a detectable level. Identical results are obtained using a microsomal fraction prepared from the 14-7fd CTL line. This observation is in complete agreement with others' data concerning the in vitro enzymatic properties of the $Sd^a$-GalNAc-transferase in human (Piller, F., et al, *Carbohydrate Res.*, Vol. 149, pp. 171–184 (1986)) and guinea pig kidney (Serafini-Cessi, F., et al, *Biochem. J.*, Vol, 215, pp. 483–489 (1983); Dall'olio, F., et al, *Bioscience Reports*, Vol. 7, pp. 925–932 (1987)), in human plasma (Takeya, A., et al, *J. Biochem.*, Vol. 101, pp. 251–259 (1987)), and the CT-GalNAc-transferase in murine cytotoxic T-lymphocyte cell lines (Conzelmann, A., et al, *J. Biol. Chem.*, Vol. 259, pp. 12528–12535 (1984); Conzelmann, A., et al, *J. Biol. Chem.*, Vol. 259, pp. 12536–12542 (1984)). In addition, microsomes prepared from pCDM8-CT transfected cells are capable of efficiently transferring GalNAc to iminobiotinylated bovine fetuin (FIG. 4), but with a substantially reduced efficiency when iminobiotinylated asialofetuin is used (FIG. 4). Similar results are obtained when microsomal preparations from 14-7fd cells are used. The apparent activity observed with the asialo substrate is most probably a function of residual activity towards the small amount of incompletely desialylated fetuin molecules contaminating the desialylated preparation.

To confirm that the enzyme activity encoded by pCDM8-CT creates the tetrasaccharide NeuAcα2,3(GalNAcβ1,4) Galβ1,4GlcNAc from the trisaccharide precursor NeuAcα2, 3Galβ1,4GlcNAc, we characterized the radiolabeled product formed from 3'-sialyl-N-acetyl-lactosamine and $^3$H-UDP-GalNAc. It was difficult to release the terminal N-acetyl-neuraminic acid from the in vitro $^3$H-GalNAc labeled product (a $t_{1/2}$ of 27 minutes, as assessed by ion-exchange HPLC) using conditions (2N acetic acid at 100° C.) that will typically yield complete release of terminal N-acetyl-neuraminic acid residues within 15 minutes (Green, E. D., et al, *J. Biol Chem.*, Vol. 263, pp. 25–35 (1988)). The terminal N-acetyl-neuraminic acid moiety on the glycolipid GM2 is similarly resistant to acid hydrolysis (Wiegant, H. in *Glycolipids* (Wiegandt, J., Ed.) pp. 199–260, Elsevier, New York, N.Y. (1985)). This resistance is apparently a consequence of the presence of a 4-O-substituted GalNAc proximal to the 3-O substituted N-acetylneuraminic acid. The neuraminic acid on the $^3$H-GalNAc labeled product was also unusually resistant to all neuraminidases we tested. The product could be partially desialylated (10–50%) by digestion with neuraminidases from *Clostridium perfringens*, *Vibrio cholera*, and Newcastle Disease virus at a concentration five-fold higher than is required to completely desialylate $^3$H-galactose labeled 3'-sialyl-N-acetyl-lactosamine.

To further characterize the product, radiolabeled material present after acid-catalyzed desialylation (2N acetic acid, 100° C., 45 minutes) was fractionated by ion-exchange HPLC (Baenziger, J. U., et al, *Anal. Biochem.*, Vol. 112, pp. 357–361 (1981)). The neutral fraction (~80% of input material) was subjected to digestion with either jack bean β-N-acetylhexoseaminidase, or with α-N-acetylhexoseaminidase. β-N-acetylhexoseaminidase digestion quantitatively released radiolabel from the desialylated product. The released radiolabel co-migrated with an N-acetylgalactosamine standard on a Bio-Rad HPX-87H organic acid HPLC column. The non-desialylated product was completely resistant to digestion with β-N-acetylhexoseaminidase. The desialylated neutral product was completely resistant to α-N-acetylhexoseaminidase digestion. Taken together, these observations demonstrate that the galactose moiety on the sialylated acceptor molecule has been substituted with GalNAc at the 4-hydroxyl, and thus supports the conclusion that the enzyme encoded by pCDM8-CT catalyzes the addition of GalNAc in β1,4-linkage to the galactose moiety of 3'-sialyl-N-acetyl-lactosamine, to form NeuAcα2,3(GalNAcβ1,4)Galβ1, 4GlcNAc.

To formally demonstrate that the present cDNA encodes the β1,4-GalNAc-transferase activity characterized above, and that it does not instead yield a tran-sacting molecule capable of generating this activity through interaction with endogenous CHO molecules, a mammalian expression vector (pPROTA-CT$_c$) that encodes a chimeric recombinant protein in which amino acid residues corresponding to the enzyme's putative catalytic domain are fused to a secretable form of the IgG binding domain of Staphylococcus aureus protein A (Sanchez-Lopez, R., et al, *J. Biol. Chem.*, Vol. 263, pp. 11892–11899 (1988)) was constructed. This vector was transfected into CHO-Tag cells and tested for its ability to generate a soluble, IgG-binding, GalNAc-transferase activity. Of the total recovered GalNAc-transferase activity produced by an aliquot of pPROTA-$CT_c$-transfected cells, 99% of the GalNAc-transferase activity was found in the culture media (Table I). Interestingly, cells transfected with the vector encoding the full-length, wild type enzyme (pCDM8-CT) also directed most of the enzyme activity to the culture media (92% of the total recovered activity; Table I), as has been observed in similar experiments with other mammalian glycosyltransferases (for example, see Kukowska-Latallo, J. F., et al, Genes & Dev., Vol. 4, pp. 1288–1303 (1990)).

The activity recovered from the media of pPROTA-$CT_c$-transfected CHO-Tag cells was applied either to an IgG-Sepharose matrix, or to a control Sepharose 4B preparation. The matrices were then thoroughly washed, and the amount of GalNAc-transferase activity present in the combined supernatant and wash fractions, or on the matrices themselves, was determined. As shown in Table IB, the activity applied to IgG-Sepharose was almost completely absorbed from the media, and 37% of the applied activity could be detected directly linked to the IgG-Sepharose beads. The activity applied to Sepharose 4B was quantitatively recovered in the supernatant and wash fraction, and no activity could be detected linked to the Sepharose beads. None of the activity generated by the plasmid vector pCDM8-CT bound to either matrix. These results demonstrate that this cloned cDNA encodes a β1,4-GalNAc-transferase and show that the peptide sequence information necessary to the enzyme's catalytic activity lies within the 476 amino acids distal to the putative trans-membrane domain.

TABLE 1

Soluble and cell-associated GalNAc-transferase activities

A. Released versus cell-associated GalNAc-transferase activity

| Vector | Cell-associated activity (units) | Released activity (units) |
|---|---|---|
| pCDM8-CT | 719.7 | 8390 (92% of total) |
| pCPROTA-$CT_c$ | 69.2 | 9828 (99% of total) |

B. Affinity chromatography of protein A-GalNAc-transferase fusion protein (pPROTA-$CT_c$) measured as units of total activity

| Chromatography matrix | applied | flowthrough | bound |
|---|---|---|---|
| Sepharose | 4914 | 4959 | none |
| Sepharose-IgG | 4914 | 214 | 1853 |

CHO-Tag cells were transfected with pCDM8-CT, or with pROTA-$CT_c$. (A) After a 68-hour expression period, media and cell extracts were assayed for GalNAc-transferase activity as described. The total activity found in cell extracts prepared from an entire plate of transfected cells is denoted "Cell-associated activity", whereas the total activity found in the processed media harvested from the same plate is termed "released activity". (B) An aliquot of the conditioned media recovered from CHO-Tag cells transfected with pPROTA-$CT_c$ was assayed to determine its content of GalNAc-transferase activity. Aliquots of media containing equal amounts of this activity ("applied" activity) were then subjected to chromatography on either Sepharose-IgG or on Sepharose 6B. GalNAc-transferase activity was determined on the material that flowed through the matrices ("flowthrough" activity), and on the material that remained bound to the matrices ("bound" activity), as described. One unit of transferase represents the amount of enzyme that can transfer one pmole of GalNAc to 189 μg of iminobiotinylated fetuin during a 90 minute incubation period, at a UDP-GalNAc concentration of 20 μM under standard assay conditions, after correction for background transfer of GalNAc to 189 μg of iminobiotinylated asialofetuin.

The CT-GalNAc-transferase shares a substantial amount of nucleotide and protein sequence identity with the human GM2/GD2 synthase.

Figure 6A:
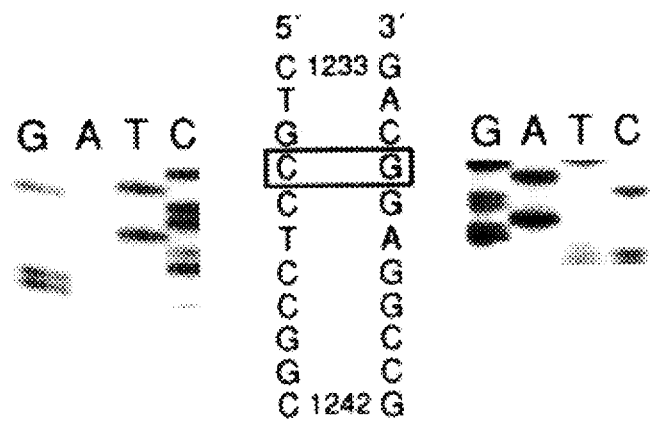
FIGS. 6A and B show the documentation of two additional cytidines in the nucleotide sequence of the human GM2/GD2 synthase. A 500-base pair DNA fragment was generated by the PCR from a human melanoma cell line (M21) cDNA library, and sequenced (see Examples below). (A) Autoradiograph of dideoxy DNA sequencing gel across the region corresponding to nucleotides 1233 to 1242, numbered according to the published sequence for the human GM2/GD2 synthase (Nagata Y., et al, *J. Biol. Chem.*, pp. 12082–12089 (1992)). The additional base pair (C-G) is delineated by a box. The sequence of the plus strand (SEQ.
Figure 6B:
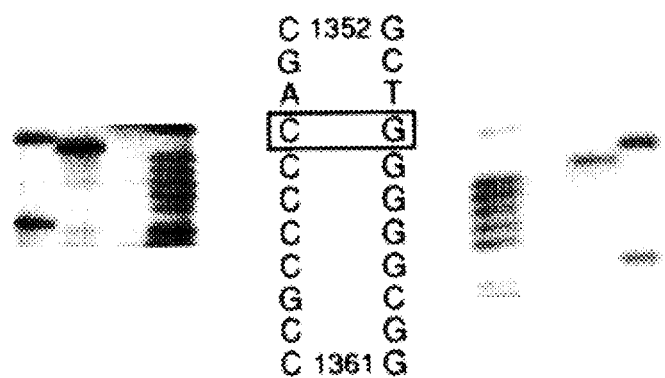

A search of the Genbank sequence database with the CT-GalNAc-transferase cDNA identified no entries with significant sequence similarity. However, we performed a direct comparison of the CT-GalNAc-transferase cDNA to a recently cloned cDNA encoding the human GM2/GD2 synthase (Nagata Y., et al, *J. Biol. Chem.*, pp. 12082–12089 (1992)), since this latter enzyme also transfers GalNAc in β1,4-linkage to the NeuAcα2,3Galβ1,4Glc-R moiety (of GM3) to generate the structure NeuAcα2,3(GalNAcβ1,4) Galβ1,4Glc-Ceramide. It was found that the CT-GalNAc-transferase maintains a substantial amount of DNA sequence identity with the human GM2/GD2 synthase cDNA (51% identity; FIGS. 5A, 5B, and 5C). The derived protein sequences of the two enzymes also share substantial amounts of protein sequence identity. We found that amino acid sequence similarity between these two proteins could be maximized by conceptually adding two bases to the published human GM2/GD2 synthase cDNA sequence, one at a position immediately after nucleotide 1295, and another immediately after nucleotide 1414 (bold type, FIGS. 5A, 5B, and 5C). To determine if these conceptual additions could be justified by correction of errors in the published human GM2/GD2 synthase cDNA sequence, we amplified a 500 nucleotide segment of the human GM2/GD2 synthase cDNA from a human melanoma cell (M21) (Mueller, B. M., et al, *Proc. Natl. Acad. Sci. U.S.A.*, Vol. 87, pp. 5702–5705 (1990)) cDNA library and determined its sequence. We found that this segment of the human GM2/GD2 synthase cDNA does contain two additional nucleotides at these positions (cytidines, in each case) (FIG. 6). Insertion of these two nucleotides yields a corrected translational reading frame for GM2/GD2 synthase that is collinear with the reading frame predicted by the CT-GalNAc-transferase cDNA, and yields a predicted GM2/GD2 synthase amino acid sequence that shares 44% identity with the murine CT-GalNAc-transferase, with maximal similarity through the regions corresponding to these enzymes' COOH-terminal catalytic domains (FIGS. 5A, 5B, and 5C).

Southern analysis of murine genomic DNA.

Figure 7:
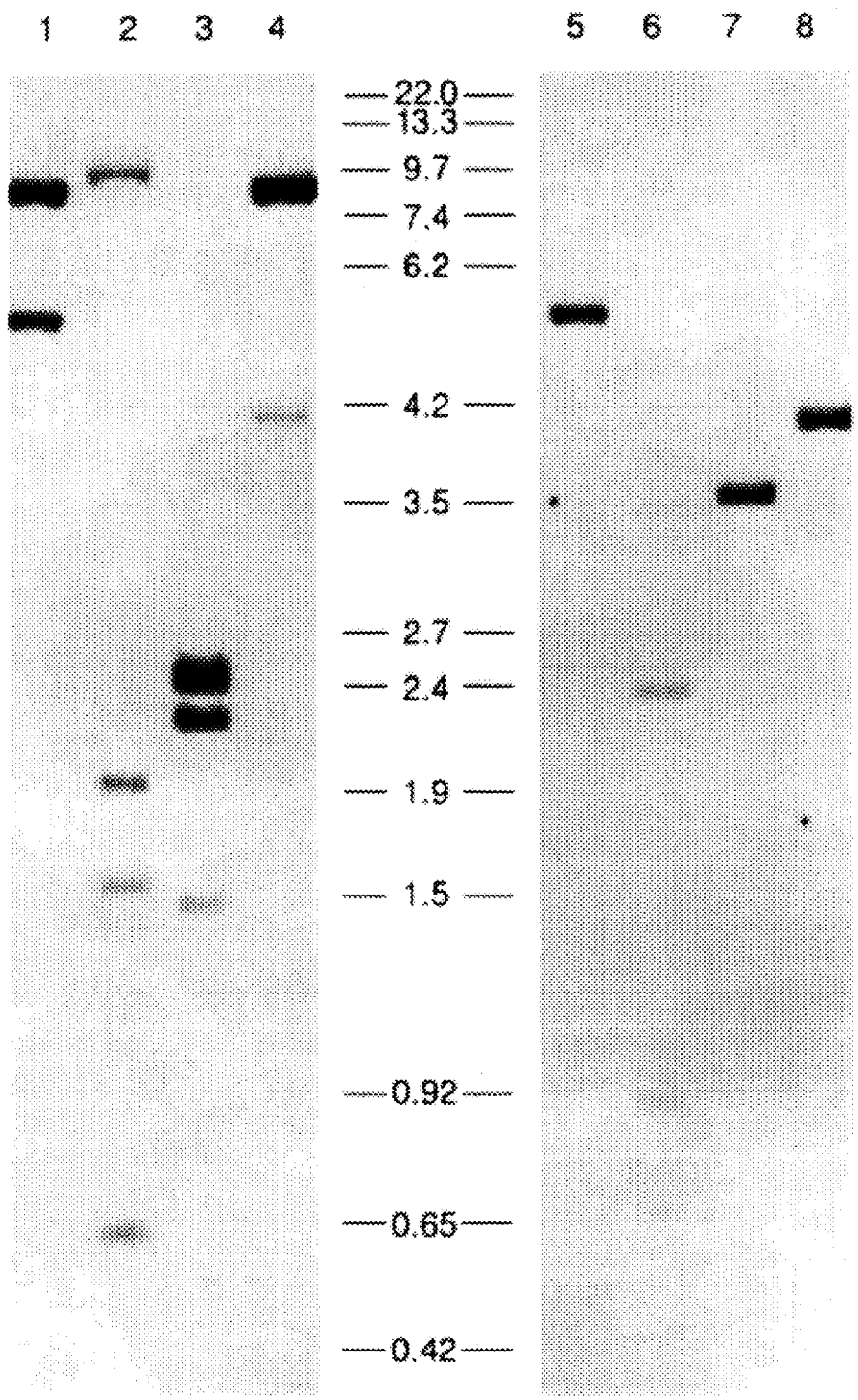
FIG. 7 illustrates the results of the Southern blot analysis of murine genomic DNA. A pair of identical blots were prepared as described in the Examples below and probed under low stringency conditions with a Bsm I-Ear I fragment of pCDM8-CT corresponding to nucleotides 523–1040 (lanes 1–4) or a PCR-amplified product of the human GM2/GD2 synthase corresponding to nucleotides 580–1144 (lanes 5–8). These regions correspond to areas of highest sequence identity (58%) between these two cDNA's. Murine genomic DNA was digested with Bam HI (lanes I and 5), Hind III (lanes 2 and 6), Pst I (lanes 3 and 7), or Eco RI (lanes 4 and 8). Molecular weight markers are shown between the two blots in kilobases.

Southern blot analyses were used to help determine if the murine CT-GalNAc-transferase cDNA corresponds to a unique gene, or if it can cross-hybridize with other similar sequences, including murine GM2/GD2 synthase gene(s). Southern blots containing murine genomic DNA were hybridized at low stringency with a probe corresponding to nucleotides 523–1090 of the CT-GalNAc-transferase cDNA or with a probe derived from the corresponding region of the human GM2/GD2 synthase cDNA (nucleotides 580–1144; FIG. 6). These two probes correspond to regions of their respective cDNAs that are most similar in nucleotide and amino acid sequence. Each probe hybridized with a unique set of DNA restriction fragments under low stringency hybridization and wash conditions, despite the substantial amount of primary sequence similarity displayed by the two probes (FIG. 7). The pattern of hybridizing fragments remained the same after washing the blots under high stringency conditions. These results demonstrate that the murine CT-GalNAc-transferase gene is distinct from a murine sequence homologous to the human GM2/GD2 synthase gene.

Obviously, numerous modifications and variations of the present invention are possible in light of the above teachings. It is therefore to be understood that, within the scope of the appended claims, the invention may be practiced otherwise than as specifically described herein.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1624 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: CDS
        ( B ) LOCATION: 42..1574

( i x ) FEATURE:
        ( A ) NAME/KEY: 5'UTR
        ( B ) LOCATION: 1..41

( x i ) SEQUENCE DESCRIPTION: SEQ ID NO:1:

```
CTGCGGTAGG CAGTCTGCAG AAGTGGCTGG AGCGAGCTGC G ATG ACT TCC AGC         53
                                              Met Thr Ser Ser
                                               1

GTG TCT TTT GCC AGC TTC AGG TTT CCA TGG CTC CTC AAG ACA TTT GTC     101
Val Ser Phe Ala Ser Phe Arg Phe Pro Trp Leu Leu Lys Thr Phe Val
  5              10                  15                  20

CTC ATG GTA GGA CTT GCC ACT GTT GCG TTT ATG GTG AGA AAG GTG TCC     149
Leu Met Val Gly Leu Ala Thr Val Ala Phe Met Val Arg Lys Val Ser
                 25                  30                  35

CTT ACA ACA GAC TTC AGC ACC TTC AAG CCA AAG TTT CCA GAG CCT GCA     197
Leu Thr Thr Asp Phe Ser Thr Phe Lys Pro Lys Phe Pro Glu Pro Ala
             40                  45                  50

AGG GTT GAC CCA GTG CTG AAG CTT CTA CCA GAG GAG CAT CTG AGG AAA     245
Arg Val Asp Pro Val Leu Lys Leu Leu Pro Glu Glu His Leu Arg Lys
         55                  60                  65

CTC TTT ACC TAC AGT GAC ATC TGG CTC TTC CCC AAA AAT CAG TGT GAC     293
Leu Phe Thr Tyr Ser Asp Ile Trp Leu Phe Pro Lys Asn Gln Cys Asp
     70                  75                  80

TGT AAC TCT GGC AAA CTG CGA ATG AAA TAT AAG TTT CAG GAT GCC TAT     341
Cys Asn Ser Gly Lys Leu Arg Met Lys Tyr Lys Phe Gln Asp Ala Tyr
 85                  90                  95                 100

AAC CAG AAG GAC CTT CCA GCT GTG AAT GCC AGA AGA CAG GCA GAA TTT     389
Asn Gln Lys Asp Leu Pro Ala Val Asn Ala Arg Arg Gln Ala Glu Phe
                105                 110                 115

GAG CAC TTT CAG AGG AGA GAA GGG CTG CCT CGC CCA CCA CCT CTG CTG     437
Glu His Phe Gln Arg Arg Glu Gly Leu Pro Arg Pro Pro Pro Leu Leu
                120                 125                 130

GCT CCA CCC AAT CTC CCC TTC GGA TAC CCA GTC CAT GGT GTG GAG GTG     485
Ala Pro Pro Asn Leu Pro Phe Gly Tyr Pro Val His Gly Val Glu Val
            135                 140                 145

ATG CCC CTG CAT ACA ATT CTC ATC CCA GGC CTC CAG TAT GAA GGG CCA     533
```

|     |     |     |     |     |     |     |     |     |     |     |     |     |     |     |      |
|-----|-----|-----|-----|-----|-----|-----|-----|-----|-----|-----|-----|-----|-----|-----|------|
| Met | Pro | Leu | His | Thr | Ile | Leu | Ile | Pro | Gly | Leu | Gln | Tyr | Glu | Gly | Pro  |
|     | 150 |     |     |     | 155 |     |     |     |     | 160 |     |     |     |     |      |
| GAT | GCT | CCA | GTC | TAT | GAG | GTC | ATC | CTG | AAA | GCT | TCT | CTG | GGG | ACA | CTG  | 581 |
| Asp | Ala | Pro | Val | Tyr | Glu | Val | Ile | Leu | Lys | Ala | Ser | Leu | Gly | Thr | Leu  |
| 165 |     |     |     |     | 170 |     |     |     |     | 175 |     |     |     |     | 180  |
| AAC | ACC | CTT | GCT | GAT | GTG | CCA | GAT | GAT | GAG | GTT | CAG | GGC | AGA | GGC | CAG  | 629 |
| Asn | Thr | Leu | Ala | Asp | Val | Pro | Asp | Asp | Glu | Val | Gln | Gly | Arg | Gly | Gln  |
|     |     |     |     | 185 |     |     |     |     | 190 |     |     |     |     | 195 |      |
| AGG | CAG | CTG | ACC | ATT | TCC | ACC | AGA | CAT | CGG | AAG | GTC | CTG | AAT | TTC | ATC  | 677 |
| Arg | Gln | Leu | Thr | Ile | Ser | Thr | Arg | His | Arg | Lys | Val | Leu | Asn | Phe | Ile  |
|     |     |     | 200 |     |     |     |     | 205 |     |     |     |     | 210 |     |      |
| CTT | CAG | CAT | GTG | ACG | TAC | ACC | AGC | ACA | GAG | TAC | TAT | CTC | CAC | AAG | GTG  | 725 |
| Leu | Gln | His | Val | Thr | Tyr | Thr | Ser | Thr | Glu | Tyr | Tyr | Leu | His | Lys | Val  |
|     |     | 215 |     |     |     |     | 220 |     |     |     |     | 225 |     |     |      |
| GAC | ACA | GTA | AGT | ATG | GAA | TAC | GAG | TCG | TCA | GTG | GCC | AAG | TTT | CCA | GTG  | 773 |
| Asp | Thr | Val | Ser | Met | Glu | Tyr | Glu | Ser | Ser | Val | Ala | Lys | Phe | Pro | Val  |
|     | 230 |     |     |     |     | 235 |     |     |     |     | 240 |     |     |     |      |
| ACT | ATC | AAA | CAA | CAG | ACT | GTA | CCC | AAG | TTG | TAT | GAC | CCT | GGA | CCT | GAG  | 821 |
| Thr | Ile | Lys | Gln | Gln | Thr | Val | Pro | Lys | Leu | Tyr | Asp | Pro | Gly | Pro | Glu  |
| 245 |     |     |     |     | 250 |     |     |     |     | 255 |     |     |     |     | 260  |
| AGG | AAG | ATC | AGA | AAC | CTG | GTG | ACC | ATT | GCC | ACG | AAG | ACT | TTT | CTC | CGT  | 869 |
| Arg | Lys | Ile | Arg | Asn | Leu | Val | Thr | Ile | Ala | Thr | Lys | Thr | Phe | Leu | Arg  |
|     |     |     |     | 265 |     |     |     |     | 270 |     |     |     |     | 275 |      |
| CCC | CAC | AAG | CTT | AAG | ATC | CTG | CTT | CAG | AGT | ATT | CGA | AAA | TAT | TAC | CCA  | 917 |
| Pro | His | Lys | Leu | Lys | Ile | Leu | Leu | Gln | Ser | Ile | Arg | Lys | Tyr | Tyr | Pro  |
|     |     |     | 280 |     |     |     |     | 285 |     |     |     |     | 290 |     |      |
| GAC | ATT | ACC | GTG | ATT | GTA | GCT | GAT | GAC | AGC | AAG | GAG | CCC | CTG | GAA | ATT  | 965 |
| Asp | Ile | Thr | Val | Ile | Val | Ala | Asp | Asp | Ser | Lys | Glu | Pro | Leu | Glu | Ile  |
|     |     | 295 |     |     |     |     | 300 |     |     |     |     | 305 |     |     |      |
| AAT | GAT | GAC | TAC | GTG | GAG | TAC | TAC | ACC | ATG | CCC | TTT | GGG | AAG | GGC | TGG  | 1013 |
| Asn | Asp | Asp | Tyr | Val | Glu | Tyr | Tyr | Thr | Met | Pro | Phe | Gly | Lys | Gly | Trp  |
|     | 310 |     |     |     |     | 315 |     |     |     |     | 320 |     |     |     |      |
| TTT | GCT | GGG | AGG | AAC | CTG | GCC | ATC | TCA | CAG | GTG | ACT | ACT | AAA | TAT | GTC  | 1061 |
| Phe | Ala | Gly | Arg | Asn | Leu | Ala | Ile | Ser | Gln | Val | Thr | Thr | Lys | Tyr | Val  |
| 325 |     |     |     |     | 330 |     |     |     |     | 335 |     |     |     |     | 340  |
| CTC | TGG | GTG | GAC | GAT | GAC | TTT | CTC | TTC | AGC | GAC | AAG | ACC | AAG | ATT | GAG  | 1109 |
| Leu | Trp | Val | Asp | Asp | Asp | Phe | Leu | Phe | Ser | Asp | Lys | Thr | Lys | Ile | Glu  |
|     |     |     |     | 345 |     |     |     |     | 350 |     |     |     |     | 355 |      |
| GTA | CTG | GTG | GAT | GTC | CTG | GAG | AAA | ACC | GAA | CTG | GAT | GTG | GTG | GGC | GGC  | 1157 |
| Val | Leu | Val | Asp | Val | Leu | Glu | Lys | Thr | Glu | Leu | Asp | Val | Val | Gly | Gly  |
|     |     |     | 360 |     |     |     |     | 365 |     |     |     |     | 370 |     |      |
| AGC | GTG | CAG | GGG | AAT | ACT | TAC | CAG | TTC | AGG | CTG | CTG | TAT | GAA | CAG | ACC  | 1205 |
| Ser | Val | Gln | Gly | Asn | Thr | Tyr | Gln | Phe | Arg | Leu | Leu | Tyr | Glu | Gln | Thr  |
|     |     | 375 |     |     |     |     | 380 |     |     |     |     | 385 |     |     |      |
| AAG | AAT | GGG | AGC | TGT | CTT | CAC | CAG | AGG | TGG | GGA | TCA | TTC | CAG | GCC | CTT  | 1253 |
| Lys | Asn | Gly | Ser | Cys | Leu | His | Gln | Arg | Trp | Gly | Ser | Phe | Gln | Ala | Leu  |
|     | 390 |     |     |     |     | 395 |     |     |     |     | 400 |     |     |     |      |
| GAC | GGC | TTT | CCC | GGA | TGC | ACG | TTG | ACC | AGC | GGC | GTG | GTG | AAC | TTC | TTC  | 1301 |
| Asp | Gly | Phe | Pro | Gly | Cys | Thr | Leu | Thr | Ser | Gly | Val | Val | Asn | Phe | Phe  |
| 405 |     |     |     |     | 410 |     |     |     |     | 415 |     |     |     |     | 420  |
| TTG | GCT | CAC | ACG | GAA | CAA | CTC | CGA | AGA | GTT | GGT | TTT | GAT | CCC | ATC | TTG  | 1349 |
| Leu | Ala | His | Thr | Glu | Gln | Leu | Arg | Arg | Val | Gly | Phe | Asp | Pro | Ile | Leu  |
|     |     |     |     | 425 |     |     |     |     | 430 |     |     |     |     | 435 |      |
| CAA | CGA | GTG | GCC | CAC | GGA | GAG | TTC | TTT | ATT | GAT | GGG | CTG | GGG | AGA | CTG  | 1397 |
| Gln | Arg | Val | Ala | His | Gly | Glu | Phe | Phe | Ile | Asp | Gly | Leu | Gly | Arg | Leu  |
|     |     |     | 440 |     |     |     |     | 445 |     |     |     |     | 450 |     |      |
| TTG | GTG | GGC | TCT | TGC | CCG | GGT | GTA | ATT | ATA | AAC | CAC | CAA | GTA | AGA | ACA  | 1445 |
| Leu | Val | Gly | Ser | Cys | Pro | Gly | Val | Ile | Ile | Asn | His | Gln | Val | Arg | Thr  |
|     |     | 455 |     |     |     |     | 460 |     |     |     |     | 465 |     |     |      |
| CCA | CCA | AAG | GAT | CCA | AAG | CTG | GCT | GCC | TTG | GAG | AAG | ACT | TAT | GAC | AAA  | 1493 |

```
Pro  Pro  Lys  Asp  Pro  Lys  Leu  Ala  Ala  Leu  Glu  Lys  Thr  Tyr  Asp  Lys
     470                 475                      480

TAC  CGG  GCC  AAC  ACC  AAT  TCT  GTG  ATC  CAA  TTC  AAG  GTT  GCA  CTC  CAG      1541
Tyr  Arg  Ala  Asn  Thr  Asn  Ser  Val  Ile  Gln  Phe  Lys  Val  Ala  Leu  Gln
485                      490                      495                      500

TAC  TTC  AAG  AAC  CAT  CTC  TAC  TGC  TCC  ACT  TAAAAAGTAC  CAAGACCAGG            1591
Tyr  Phe  Lys  Asn  His  Leu  Tyr  Cys  Ser  Thr
                    505                      510

AATCGCAATA  AACAGATTAG  CGGCGGGCAA  CAA                                              1624
```

( 2 ) INFORMATION FOR SEQ ID NO:2:

( i ) SEQUENCE CHARACTERISTICS:
        ( A ) LENGTH: 510 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Ser  Ser  Val  Ser  Phe  Ala  Ser  Phe  Arg  Phe  Pro  Trp  Leu  Leu
1                       5                       10                      15

Lys  Thr  Phe  Val  Leu  Met  Val  Gly  Leu  Ala  Thr  Val  Ala  Phe  Met  Val
               20                      25                      30

Arg  Lys  Val  Ser  Leu  Thr  Thr  Asp  Phe  Ser  Thr  Phe  Lys  Pro  Lys  Phe
          35                      40                      45

Pro  Glu  Pro  Ala  Arg  Val  Asp  Pro  Val  Leu  Lys  Leu  Leu  Pro  Glu  Glu
     50                      55                      60

His  Leu  Arg  Lys  Leu  Phe  Thr  Tyr  Ser  Asp  Ile  Trp  Leu  Phe  Pro  Lys
65                       70                      75                      80

Asn  Gln  Cys  Asp  Cys  Asn  Ser  Gly  Lys  Leu  Arg  Met  Lys  Tyr  Lys  Phe
                    85                      90                      95

Gln  Asp  Ala  Tyr  Asn  Gln  Lys  Asp  Leu  Pro  Ala  Val  Asn  Ala  Arg  Arg
               100                     105                     110

Gln  Ala  Glu  Phe  Glu  His  Phe  Gln  Arg  Arg  Glu  Gly  Leu  Pro  Arg  Pro
          115                     120                     125

Pro  Pro  Leu  Leu  Ala  Pro  Pro  Asn  Leu  Pro  Phe  Gly  Tyr  Pro  Val  His
     130                     135                     140

Gly  Val  Glu  Val  Met  Pro  Leu  His  Thr  Ile  Leu  Ile  Pro  Gly  Leu  Gln
145                      150                     155                     160

Tyr  Glu  Gly  Pro  Asp  Ala  Pro  Val  Tyr  Glu  Val  Ile  Leu  Lys  Ala  Ser
                    165                     170                     175

Leu  Gly  Thr  Leu  Asn  Thr  Leu  Ala  Asp  Val  Pro  Asp  Asp  Glu  Val  Gln
               180                     185                     190

Gly  Arg  Gly  Gln  Arg  Gln  Leu  Thr  Ile  Ser  Thr  Arg  His  Arg  Lys  Val
          195                     200                     205

Leu  Asn  Phe  Ile  Leu  Gln  His  Val  Thr  Tyr  Thr  Ser  Thr  Glu  Tyr  Tyr
     210                     215                     220

Leu  His  Lys  Val  Asp  Thr  Val  Ser  Met  Glu  Tyr  Glu  Ser  Ser  Val  Ala
225                      230                     235                     240

Lys  Phe  Pro  Val  Thr  Ile  Lys  Gln  Gln  Thr  Val  Pro  Lys  Leu  Tyr  Asp
                    245                     250                     255

Pro  Gly  Pro  Glu  Arg  Lys  Ile  Arg  Asn  Leu  Val  Thr  Ile  Ala  Thr  Lys
               260                     265                     270

Thr  Phe  Leu  Arg  Pro  His  Lys  Leu  Lys  Ile  Leu  Leu  Gln  Ser  Ile  Arg
          275                     280                     285

Lys  Tyr  Tyr  Pro  Asp  Ile  Thr  Val  Ile  Val  Ala  Asp  Asp  Ser  Lys  Glu
```

|     |     |     |     |     | 290 |     |     |     |     | 295 |     |     |     |     | 300 |     |     |     |     |
|-----|-----|-----|-----|-----|-----|-----|-----|-----|-----|-----|-----|-----|-----|-----|-----|-----|-----|-----|-----|
| Pro | Leu | Glu | Ile | Asn | Asp | Asp | Tyr | Val | Glu | Tyr | Tyr | Thr | Met | Pro | Phe |
| 305 |     |     |     |     | 310 |     |     |     |     | 315 |     |     |     |     | 320 |

Gly Lys Gly Trp Phe Ala Gly Arg Asn Leu Ala Ile Ser Gln Val Thr
                    325                 330                 335

Thr Lys Tyr Val Leu Trp Val Asp Asp Phe Leu Phe Ser Asp Lys
            340                 345                 350

Thr Lys Ile Glu Val Leu Val Asp Val Leu Glu Lys Thr Glu Leu Asp
            355                 360                 365

Val Val Gly Gly Ser Val Gln Gly Asn Thr Tyr Gln Phe Arg Leu Leu
    370                 375                 380

Tyr Glu Gln Thr Lys Asn Gly Ser Cys Leu His Gln Arg Trp Gly Ser
385                 390                 395                 400

Phe Gln Ala Leu Asp Gly Phe Pro Gly Cys Thr Leu Thr Ser Gly Val
            405                 410                 415

Val Asn Phe Phe Leu Ala His Thr Glu Gln Leu Arg Arg Val Gly Phe
            420                 425                 430

Asp Pro Ile Leu Gln Arg Val Ala His Gly Glu Phe Phe Ile Asp Gly
            435                 440                 445

Leu Gly Arg Leu Leu Val Gly Ser Cys Pro Gly Val Ile Ile Asn His
    450                 455                 460

Gln Val Arg Thr Pro Pro Lys Asp Pro Lys Leu Ala Ala Leu Glu Lys
465                 470                 475                 480

Thr Tyr Asp Lys Tyr Arg Ala Asn Thr Asn Ser Val Ile Gln Phe Lys
            485                 490                 495

Val Ala Leu Gln Tyr Phe Lys Asn His Leu Tyr Cys Ser Thr
            500                 505                 510

( 2 ) INFORMATION FOR SEQ ID NO:3:

( i ) SEQUENCE CHARACTERISTICS:
      ( A ) LENGTH: 1086 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 1..1086

( x i ) SEQUENCE DESCRIPTION: SEQ ID NO:3:

```
GCC TAT AAC CAG AAG GAC CTT CCA GCT GTG AAT GCC AGA AGA CAG GCA       48
Ala Tyr Asn Gln Lys Asp Leu Pro Ala Val Asn Ala Arg Arg Gln Ala
 1               5                  10                  15

GAA TTT GAG CAC TTT CAG AGG AGA GAA GGG CTG CCT CGC CCA CCA CCT       96
Glu Phe Glu His Phe Gln Arg Arg Glu Gly Leu Pro Arg Pro Pro Pro
             20                  25                  30

CTG CTG GCT CCA CCC AAT CTC CCC TTC GGA TAC CCA GTC CAT GGT GTG      144
Leu Leu Ala Pro Pro Asn Leu Pro Phe Gly Tyr Pro Val His Gly Val
         35                  40                  45

GAG GTG ATG CCC CTG CAT ACA ATT CTC ATC CCA GGC CTC CAG TAT GAA      192
Glu Val Met Pro Leu His Thr Ile Leu Ile Pro Gly Leu Gln Tyr Glu
     50                  55                  60

GGG CCA GAT GCT CCA GTC TAT GAG GTC ATC CTG AAA GCT TCT CTG GGG      240
Gly Pro Asp Ala Pro Val Tyr Glu Val Ile Leu Lys Ala Ser Leu Gly
 65                  70                  75                  80

ACA CTG AAC ACC CTT GCT GAT GTG CCA GAT GAT GAG GTT CAG GGC AGA      288
Thr Leu Asn Thr Leu Ala Asp Val Pro Asp Asp Glu Val Gln Gly Arg
```

|       |       |       |       |       |       |       | 85    |       |       |       |       | 90    |       |       |       |       | 95    |       |       |      |
|-------|-------|-------|-------|-------|-------|-------|-------|-------|-------|-------|-------|-------|-------|-------|-------|-------|-------|-------|-------|------|
| GGC   | CAG   | AGG   | CAG   | CTG   | ACC   | ATT   | TCC   | ACC   | AGA   | CAT   | CGG   | AAG   | GTC   | CTG   | AAT   |       |       |       |       | 336  |
| Gly   | Gln   | Arg   | Gln   | Leu   | Thr   | Ile   | Ser   | Thr   | Arg   | His   | Arg   | Lys   | Val   | Leu   | Asn   |       |       |       |       |      |
|       |       |       | 100   |       |       |       |       | 105   |       |       |       | 110   |       |       |       |       |       |       |       |      |

| TTC | ATC | CTT | CAG | CAT | GTG | ACG | TAC | ACC | AGC | ACA | GAG | TAC | TAT | CTC | CAC | 384 |
|-----|-----|-----|-----|-----|-----|-----|-----|-----|-----|-----|-----|-----|-----|-----|-----|-----|
| Phe | Ile | Leu | Gln | His | Val | Thr | Tyr | Thr | Ser | Thr | Glu | Tyr | Tyr | Leu | His |     |
|     |     | 115 |     |     |     |     | 120 |     |     |     |     | 125 |     |     |     |     |

| AAG | GTG | GAC | ACA | GTA | AGT | ATG | GAA | TAC | GAG | TCG | TCA | GTG | GCC | AAG | TTT | 432 |
| Lys | Val | Asp | Thr | Val | Ser | Met | Glu | Tyr | Glu | Ser | Ser | Val | Ala | Lys | Phe |     |
|     | 130 |     |     |     |     | 135 |     |     |     |     | 140 |     |     |     |     |     |

| CCA | GTG | ACT | ATC | AAA | CAA | CAG | ACT | GTA | CCC | AAG | TTG | TAT | GAC | CCT | GGA | 480 |
| Pro | Val | Thr | Ile | Lys | Gln | Gln | Thr | Val | Pro | Lys | Leu | Tyr | Asp | Pro | Gly |     |
| 145 |     |     |     |     | 150 |     |     |     |     | 155 |     |     |     |     | 160 |     |

| CCT | GAG | AGG | AAG | ATC | AGA | AAC | CTG | GTG | ACC | ATT | GCC | ACG | AAG | ACT | TTT | 528 |
| Pro | Glu | Arg | Lys | Ile | Arg | Asn | Leu | Val | Thr | Ile | Ala | Thr | Lys | Thr | Phe |     |
|     |     |     |     | 165 |     |     |     |     | 170 |     |     |     |     | 175 |     |     |

| CTC | CGT | CCC | CAC | AAG | CTT | AAG | ATC | CTG | CTT | CAG | AGT | ATT | CGA | AAA | TAT | 576 |
| Leu | Arg | Pro | His | Lys | Leu | Lys | Ile | Leu | Leu | Gln | Ser | Ile | Arg | Lys | Tyr |     |
|     |     |     | 180 |     |     |     |     | 185 |     |     |     | 190 |     |     |     |     |

| TAC | CCA | GAC | ATT | ACC | GTG | ATT | GTA | GCT | GAT | GAC | AGC | AAG | GAG | CCC | CTG | 624 |
| Tyr | Pro | Asp | Ile | Thr | Val | Ile | Val | Ala | Asp | Asp | Ser | Lys | Glu | Pro | Leu |     |
|     |     | 195 |     |     |     |     | 200 |     |     |     |     | 205 |     |     |     |     |

| GAA | ATT | AAT | GAT | GAC | TAC | GTG | GAG | TAC | TAC | ACC | ATG | CCC | TTT | GGG | AAG | 672 |
| Glu | Ile | Asn | Asp | Asp | Tyr | Val | Glu | Tyr | Tyr | Thr | Met | Pro | Phe | Gly | Lys |     |
|     | 210 |     |     |     |     | 215 |     |     |     |     | 220 |     |     |     |     |     |

| GGC | TGG | TTT | GCT | GGG | AGG | AAC | CTG | GCC | ATC | TCA | CAG | GTG | ACT | ACT | AAA | 720 |
| Gly | Trp | Phe | Ala | Gly | Arg | Asn | Leu | Ala | Ile | Ser | Gln | Val | Thr | Thr | Lys |     |
| 225 |     |     |     |     | 230 |     |     |     |     | 235 |     |     |     |     | 240 |     |

| TAT | GTC | CTC | TGG | GTG | GAC | GAT | GAC | TTT | CTC | TTC | AGC | GAC | AAG | ACC | AAG | 768 |
| Tyr | Val | Leu | Trp | Val | Asp | Asp | Asp | Phe | Leu | Phe | Ser | Asp | Lys | Thr | Lys |     |
|     |     |     |     | 245 |     |     |     |     | 250 |     |     |     |     | 255 |     |     |

| ATT | GAG | GTA | CTG | GTG | GAT | GTC | CTG | GAG | AAA | ACC | GAA | CTG | GAT | GTG | GTG | 816 |
| Ile | Glu | Val | Leu | Val | Asp | Val | Leu | Glu | Lys | Thr | Glu | Leu | Asp | Val | Val |     |
|     |     |     | 260 |     |     |     |     | 265 |     |     |     |     | 270 |     |     |     |

| GGC | GGC | AGC | GTG | CAG | GGG | AAT | ACT | TAC | CAG | TTC | AGG | CTG | CTG | TAT | GAA | 864 |
| Gly | Gly | Ser | Val | Gln | Gly | Asn | Thr | Tyr | Gln | Phe | Arg | Leu | Leu | Tyr | Glu |     |
|     |     | 275 |     |     |     |     | 280 |     |     |     |     | 285 |     |     |     |     |

| CAG | ACC | AAG | AAT | GGG | AGC | TGT | CTT | CAC | CAG | AGG | TGG | GGA | TCA | TTC | CAG | 912 |
| Gln | Thr | Lys | Asn | Gly | Ser | Cys | Leu | His | Gln | Arg | Trp | Gly | Ser | Phe | Gln |     |
|     | 290 |     |     |     |     | 295 |     |     |     |     | 300 |     |     |     |     |     |

| GCC | CTT | GAC | GGC | TTT | CCC | GGA | TGC | ACG | TTG | ACC | AGC | GGC | GTG | GTG | AAC | 960 |
| Ala | Leu | Asp | Gly | Phe | Pro | Gly | Cys | Thr | Leu | Thr | Ser | Gly | Val | Val | Asn |     |
| 305 |     |     |     |     | 310 |     |     |     |     | 315 |     |     |     |     | 320 |     |

| TTC | TTC | TTG | GCT | CAC | ACG | GAA | CAA | CTC | CGA | AGA | GTT | GGT | TTT | GAT | CCC | 1008 |
| Phe | Phe | Leu | Ala | His | Thr | Glu | Gln | Leu | Arg | Arg | Val | Gly | Phe | Asp | Pro |      |
|     |     |     |     | 325 |     |     |     |     | 330 |     |     |     |     | 335 |     |      |

| ATC | TTG | CAA | CGA | GTG | GCC | CAC | GGA | GAG | TTC | TTT | ATT | GAT | GGG | CTG | GGG | 1056 |
| Ile | Leu | Gln | Arg | Val | Ala | His | Gly | Glu | Phe | Phe | Ile | Asp | Gly | Leu | Gly |      |
|     |     |     | 340 |     |     |     |     | 345 |     |     |     |     | 350 |     |     |      |

| AGA | CTG | TTG | GTG | GGC | TCT | TGC | CCG | GGT | GTA | 1086 |
| Arg | Leu | Leu | Val | Gly | Ser | Cys | Pro | Gly | Val |      |
|     |     | 355 |     |     |     |     | 360 |     |     |      |

( 2 ) INFORMATION FOR SEQ ID NO:4:

( i ) SEQUENCE CHARACTERISTICS:
        ( A ) LENGTH: 362 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ala | Tyr | Asn | Gln | Lys | Asp | Leu | Pro | Ala | Val | Asn | Ala | Arg | Arg | Gln | Ala |
|---|---|---|---|---|---|---|---|---|---|---|---|---|---|---|---|
| 1 | | | | 5 | | | | | 10 | | | | | 15 | |

| Glu | Phe | Glu | His | Phe | Gln | Arg | Arg | Glu | Gly | Leu | Pro | Arg | Pro | Pro | Pro |
| | | | 20 | | | | | 25 | | | | | 30 | | |

| Leu | Leu | Ala | Pro | Pro | Asn | Leu | Pro | Phe | Gly | Tyr | Pro | Val | His | Gly | Val |
| | | 35 | | | | | 40 | | | | | 45 | | | |

| Glu | Val | Met | Pro | Leu | His | Thr | Ile | Leu | Ile | Pro | Gly | Leu | Gln | Tyr | Glu |
| | 50 | | | | | 55 | | | | | 60 | | | | |

| Gly | Pro | Asp | Ala | Pro | Val | Tyr | Glu | Val | Ile | Leu | Lys | Ala | Ser | Leu | Gly |
| 65 | | | | | 70 | | | | | 75 | | | | | 80 |

| Thr | Leu | Asn | Thr | Leu | Ala | Asp | Val | Pro | Asp | Asp | Glu | Val | Gln | Gly | Arg |
| | | | | 85 | | | | | 90 | | | | | 95 | |

| Gly | Gln | Arg | Gln | Leu | Thr | Ile | Ser | Thr | Arg | His | Arg | Lys | Val | Leu | Asn |
| | | | 100 | | | | | 105 | | | | | 110 | | |

| Phe | Ile | Leu | Gln | His | Val | Thr | Tyr | Thr | Ser | Thr | Glu | Tyr | Tyr | Leu | His |
| | | | 115 | | | | | 120 | | | | | 125 | | |

| Lys | Val | Asp | Thr | Val | Ser | Met | Glu | Tyr | Glu | Ser | Ser | Val | Ala | Lys | Phe |
| | 130 | | | | | 135 | | | | | 140 | | | | |

| Pro | Val | Thr | Ile | Lys | Gln | Gln | Thr | Val | Pro | Lys | Leu | Tyr | Asp | Pro | Gly |
| 145 | | | | | 150 | | | | | 155 | | | | | 160 |

| Pro | Glu | Arg | Lys | Ile | Arg | Asn | Leu | Val | Thr | Ile | Ala | Thr | Lys | Thr | Phe |
| | | | | 165 | | | | | 170 | | | | | 175 | |

| Leu | Arg | Pro | His | Lys | Leu | Lys | Ile | Leu | Leu | Gln | Ser | Ile | Arg | Lys | Tyr |
| | | | 180 | | | | | 185 | | | | | 190 | | |

| Tyr | Pro | Asp | Ile | Thr | Val | Ile | Val | Ala | Asp | Asp | Ser | Lys | Glu | Pro | Leu |
| | | 195 | | | | | 200 | | | | | 205 | | | |

| Glu | Ile | Asn | Asp | Asp | Tyr | Val | Glu | Tyr | Tyr | Thr | Met | Pro | Phe | Gly | Lys |
| | 210 | | | | | 215 | | | | | 220 | | | | |

| Gly | Trp | Phe | Ala | Gly | Arg | Asn | Leu | Ala | Ile | Ser | Gln | Val | Thr | Thr | Lys |
| 225 | | | | | 230 | | | | | 235 | | | | | 240 |

| Tyr | Val | Leu | Trp | Val | Asp | Asp | Asp | Phe | Leu | Phe | Ser | Asp | Lys | Thr | Lys |
| | | | | 245 | | | | | 250 | | | | | 255 | |

| Ile | Glu | Val | Leu | Val | Asp | Val | Leu | Glu | Lys | Thr | Glu | Leu | Asp | Val | Val |
| | | | 260 | | | | | 265 | | | | | 270 | | |

| Gly | Gly | Ser | Val | Gln | Gly | Asn | Thr | Tyr | Gln | Phe | Arg | Leu | Leu | Tyr | Glu |
| | | 275 | | | | | 280 | | | | | 285 | | | |

| Gln | Thr | Lys | Asn | Gly | Ser | Cys | Leu | His | Gln | Arg | Trp | Gly | Ser | Phe | Gln |
| | 290 | | | | | 295 | | | | | 300 | | | | |

| Ala | Leu | Asp | Gly | Phe | Pro | Gly | Cys | Thr | Leu | Thr | Ser | Gly | Val | Val | Asn |
| 305 | | | | | 310 | | | | | 315 | | | | | 320 |

| Phe | Phe | Leu | Ala | His | Thr | Glu | Gln | Leu | Arg | Arg | Val | Gly | Phe | Asp | Pro |
| | | | | 325 | | | | | 330 | | | | | 335 | |

| Ile | Leu | Gln | Arg | Val | Ala | His | Gly | Glu | Phe | Phe | Ile | Asp | Gly | Leu | Gly |
| | | | 340 | | | | | 345 | | | | | 350 | | |

| Arg | Leu | Leu | Val | Gly | Ser | Cys | Pro | Gly | Val |
| | | | 355 | | | | 360 | | |

( 2 ) INFORMATION FOR SEQ ID NO:5:

( i ) SEQUENCE CHARACTERISTICS:
( A ) LENGTH: 1125 base pairs
( B ) TYPE: nucleic acid
( C ) STRANDEDNESS: single
( D ) TOPOLOGY: linear ( i i ) MOLECULE TYPE: cDNA ( i x ) FEATURE:
    ( A ) NAME/KEY: CDS
    ( B ) LOCATION: 1..1125

( x i ) SEQUENCE DESCRIPTION: SEQ ID NO:5:

```
GCC TTT GAC CCT GCA GAG CTG AGG GCT GCC TCT GCC ACA AGA GAG CAG    48
Ala Phe Asp Pro Ala Glu Leu Arg Ala Ala Ser Ala Thr Arg Glu Gln
 1               5                  10                  15

GAG TTC CAG GCC TTT CTG TCG AGG AGC CAG TCC CCA GCT GAC CAG CTG    96
Glu Phe Gln Ala Phe Leu Ser Arg Ser Gln Ser Pro Ala Asp Gln Leu
            20                  25                  30

CTC ATA GCC CCT GCC AAC TCC CCG CTC CAG TAC CCC CTA CAG GGT GTG   144
Leu Ile Ala Pro Ala Asn Ser Pro Leu Gln Tyr Pro Leu Gln Gly Val
        35                  40                  45

GAA GTT CAG CCC CTC AGG AGC ATC TTG GTG CCA GGG CTG AGC CTT CAG   192
Glu Val Gln Pro Leu Arg Ser Ile Leu Val Pro Gly Leu Ser Leu Gln
50                  55                  60

GCA GCT TCT GGT CAG GAG GTA TAC CAG GTG AAC CTG ACT GCC TCC CTA   240
Ala Ala Ser Gly Gln Glu Val Tyr Gln Val Asn Leu Thr Ala Ser Leu
65                  70                  75                  80

GGC ACC TGG GAC GTG GCA GGG GAA GTG ACT GGA GTT ACT CTC ACT GGA   288
Gly Thr Trp Asp Val Ala Gly Glu Val Thr Gly Val Thr Leu Thr Gly
                85                  90                  95

GAG GGT CAG GCA GAT CTC ACC CTT GTC AGC CCA GGG CTG GAC CAA CTC   336
Glu Gly Gln Ala Asp Leu Thr Leu Val Ser Pro Gly Leu Asp Gln Leu
            100                 105                 110

AAC AGG CAA CTA CAA CTG GTC ACT TAC AGC AGC CGA AGC TAC CAG ACC   384
Asn Arg Gln Leu Gln Leu Val Thr Tyr Ser Ser Arg Ser Tyr Gln Thr
        115                 120                 125

AAC ACA GCA GAC ACA GTC CGG TTC TCC ACC GAG GGA CAT GAG GCT GCT   432
Asn Thr Ala Asp Thr Val Arg Phe Ser Thr Glu Gly His Glu Ala Ala
130                 135                 140

TTC ACT ATC CGC ATA AGA CAC CCG CCC AAC CCT CGG CTG TAC CCA CCT   480
Phe Thr Ile Arg Ile Arg His Pro Pro Asn Pro Arg Leu Tyr Pro Pro
145                 150                 155                 160

GGG TCT CTA CCC CAG GGA GCC CAG TAC AAC ATC AGC GCT CTA GTC ACG   528
Gly Ser Leu Pro Gln Gly Ala Gln Tyr Asn Ile Ser Ala Leu Val Thr
                165                 170                 175

ATT GCC ACC AAG ACC TTC CTC CGT TAT GAT CGG CTA CGG GCT CTC ATC   576
Ile Ala Thr Lys Thr Phe Leu Arg Tyr Asp Arg Leu Arg Ala Leu Ile
            180                 185                 190

ACC AGT ATC CGC CGC TTC TAC CCA ACG GTT ACC GTG GTC ATC GCT GAC   624
Thr Ser Ile Arg Arg Phe Tyr Pro Thr Val Thr Val Val Ile Ala Asp
        195                 200                 205

GAC AGC GAC AAG CCA GAG CGC GTT AGT GGC CCC TAC GTG GAA CAC TAT   672
Asp Ser Asp Lys Pro Glu Arg Val Ser Gly Pro Tyr Val Glu His Tyr
210                 215                 220

CTC ATG CCC TTC GGC AAG GGC TGG TTC GCA GGC CGG AAC CTG GCC GTG   720
Leu Met Pro Phe Gly Lys Gly Trp Phe Ala Gly Arg Asn Leu Ala Val
225                 230                 235                 240

TCT CAA GTA ACC ACC AAG TAC GTG CTG TGG GTG GAC GAC GAC TTC GTC   768
Ser Gln Val Thr Thr Lys Tyr Val Leu Trp Val Asp Asp Asp Phe Val
                245                 250                 255

TTC ACG GCG CGG ACG CGG CTG GAG AGG CTT GTG GAC GTG CTG GAG CGG   816
Phe Thr Ala Arg Thr Arg Leu Glu Arg Leu Val Asp Val Leu Glu Arg
            260                 265                 270

ACG CCG CTG GAC CTG GTG GGG GGC GCG GTG CGC GAG ATC TCC GGC TTT   864
Thr Pro Leu Asp Leu Val Gly Gly Ala Val Arg Glu Ile Ser Gly Phe
        275                 280                 285
```

```
GCC  ACC  ACT  TAT  CGG  CAG  CTG  CTG  AGC  GTG  GAG  CCC  GGC  GCC  CCA  GGC        912
Ala  Thr  Thr  Tyr  Arg  Gln  Leu  Leu  Ser  Val  Glu  Pro  Gly  Ala  Pro  Gly
290                      295                      300

CTC  GGG  AAC  TGC  CTC  CGG  CAA  AGG  CGC  GGC  TTC  CAC  CAC  GAG  CTC  GTC        960
Leu  Gly  Asn  Cys  Leu  Arg  Gln  Arg  Arg  Gly  Phe  His  His  Glu  Leu  Val
305                      310                      315                      320

GGC  TTC  CCA  GGC  TGC  GTG  GTC  ACC  GAC  GGC  GTG  GTT  AAC  TTC  TTC  CTG       1008
Gly  Phe  Pro  Gly  Cys  Val  Val  Thr  Asp  Gly  Val  Val  Asn  Phe  Phe  Leu
                325                      330                      335

GCG  CGG  ACT  GAC  AAG  GTG  CGC  GAG  GTC  GGT  TTC  GAC  CCC  CGC  CTC  AGC       1056
Ala  Arg  Thr  Asp  Lys  Val  Arg  Glu  Val  Gly  Phe  Asp  Pro  Arg  Leu  Ser
               340                      345                      350

CGC  GTG  GCT  CAT  CTG  GAA  TTC  TTC  TTG  GAT  GGG  CTT  GGT  TCC  CTT  CGG       1104
Arg  Val  Ala  His  Leu  Glu  Phe  Phe  Leu  Asp  Gly  Leu  Gly  Ser  Leu  Arg
          355                      360                      365

GTT  GGC  TCC  TGC  TCC  GAC  GTC                                                    1125
Val  Gly  Ser  Cys  Ser  Asp  Val
370                      375
```

( 2 ) INFORMATION FOR SEQ ID NO:6:

( i ) SEQUENCE CHARACTERISTICS:
        ( A ) LENGTH: 375 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Ala  Phe  Asp  Pro  Ala  Glu  Leu  Arg  Ala  Ala  Ser  Ala  Thr  Arg  Glu  Gln
1                   5                   10                      15

Glu  Phe  Gln  Ala  Phe  Leu  Ser  Arg  Ser  Gln  Ser  Pro  Ala  Asp  Gln  Leu
               20                      25                      30

Leu  Ile  Ala  Pro  Ala  Asn  Ser  Pro  Leu  Gln  Tyr  Pro  Leu  Gln  Gly  Val
          35                      40                      45

Glu  Val  Gln  Pro  Leu  Arg  Ser  Ile  Leu  Val  Pro  Gly  Leu  Ser  Leu  Gln
     50                      55                      60

Ala  Ala  Ser  Gly  Gln  Glu  Val  Tyr  Gln  Val  Asn  Leu  Thr  Ala  Ser  Leu
65                      70                      75                           80

Gly  Thr  Trp  Asp  Val  Ala  Gly  Glu  Val  Thr  Gly  Val  Thr  Leu  Thr  Gly
               85                      90                      95

Glu  Gly  Gln  Ala  Asp  Leu  Thr  Leu  Val  Ser  Pro  Gly  Leu  Asp  Gln  Leu
               100                     105                     110

Asn  Arg  Gln  Leu  Gln  Leu  Val  Thr  Tyr  Ser  Ser  Arg  Ser  Tyr  Gln  Thr
          115                     120                     125

Asn  Thr  Ala  Asp  Thr  Val  Arg  Phe  Ser  Thr  Glu  Gly  His  Glu  Ala  Ala
     130                     135                     140

Phe  Thr  Ile  Arg  Ile  Arg  His  Pro  Pro  Asn  Pro  Arg  Leu  Tyr  Pro  Pro
145                     150                     155                         160

Gly  Ser  Leu  Pro  Gln  Gly  Ala  Gln  Tyr  Asn  Ile  Ser  Ala  Leu  Val  Thr
               165                     170                     175

Ile  Ala  Thr  Lys  Thr  Phe  Leu  Arg  Tyr  Asp  Arg  Leu  Arg  Ala  Leu  Ile
               180                     185                     190

Thr  Ser  Ile  Arg  Arg  Phe  Tyr  Pro  Thr  Val  Thr  Val  Ile  Ala  Asp
          195                     200                     205

Asp  Ser  Asp  Lys  Pro  Glu  Arg  Val  Ser  Gly  Pro  Tyr  Val  Glu  His  Tyr
     210                     215                     220

Leu  Met  Pro  Phe  Gly  Lys  Gly  Trp  Phe  Ala  Gly  Arg  Asn  Leu  Ala  Val
225                     230                     235                         240
```

```
Ser Gln Val Thr Thr Lys Tyr Val Leu Trp Val Asp Asp Asp Phe Val
            245                 250                 255

Phe Thr Ala Arg Thr Arg Leu Glu Arg Leu Val Asp Val Leu Glu Arg
            260                 265                 270

Thr Pro Leu Asp Leu Val Gly Gly Ala Val Arg Glu Ile Ser Gly Phe
            275                 280                 285

Ala Thr Thr Tyr Arg Gln Leu Leu Ser Val Glu Pro Gly Ala Pro Gly
            290                 295                 300

Leu Gly Asn Cys Leu Arg Gln Arg Arg Gly Phe His His Glu Leu Val
305                 310                 315                 320

Gly Phe Pro Gly Cys Val Val Thr Asp Gly Val Val Asn Phe Phe Leu
                325                 330                 335

Ala Arg Thr Asp Lys Val Arg Glu Val Gly Phe Asp Pro Arg Leu Ser
                340                 345                 350

Arg Val Ala His Leu Glu Phe Phe Leu Asp Gly Leu Gly Ser Leu Arg
            355                 360                 365

Val Gly Ser Cys Ser Asp Val
370                 375
```

( 2 ) INFORMATION FOR SEQ ID NO:7:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:7:

```
GCGCCTCGAG GTATACCAGG TGAACCTGAC TGCCTCC                    37
```

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:8:

```
GCGCTCGAGT GAAGACGAAG TCGTCGTCCA CCC                        33
```

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:9:

```
GCGCTCGAGC CACTTATCGG CAGCTGCTGA GCGTGGAGC                  39
```

( 2 ) INFORMATION FOR SEQ ID NO:10:

( i ) SEQUENCE CHARACTERISTICS:
        ( A ) LENGTH: 37 base pairs
        ( B ) TYPE: nucleic acid
        ( C ) STRANDEDNESS: single (D) TOPOLOGY: linear (ii) MOLECULE TYPE: Other nucleic acid (xi) SEQUENCE DESCRIPTION: SEQ ID NO:10:

GCGCCTCGAG TGCTCACAGG GTGGTGGGGT TTGTTGG                37

(2) INFORMATION FOR SEQ ID NO:11:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:11:

CGCGAATTCG GTGTCCCTTA CAACAGACTT CAGCACC                37

(2) INFORMATION FOR SEQ ID NO:12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:12:

CGCGAATTCG GTACTTTTA AGTGGAGCAG TAGAGATGG                39

(2) INFORMATION FOR SEQ ID NO:13:

(i) SEQUENCE CHARACTERISTICS:
        (A) LENGTH: 11 base pairs
        (B) TYPE: nucleic acid
        (C) STRANDEDNESS: double
        (D) TOPOLOGY: linear (xi) SEQUENCE DESCRIPTION: SEQ ID NO:13:

CTGCCTCCGG C                11

(2) INFORMATION FOR SEQ ID NO:14:

(i) SEQUENCE CHARACTERISTICS:
        (A) LENGTH: 11 base pairs
        (B) TYPE: nucleic acid
        (C) STRANDEDNESS: double
        (D) TOPOLOGY: linear (xi) SEQUENCE DESCRIPTION: SEQ ID NO:14:

CGACCCCCGC C                11

What is claimed as new and is desired to be secured by Letters Patent of the United States is:

1. An isolated sequence of DNA which encodes a polypeptide having an amino acid sequence selected from the group consisting of:

(a) from position 35 to position 510 of the amino acid sequence of SEQ ID NO: 2; and (b) from position 1 to position 510 of the amino acid sequence of SEQ ID NO: 2.

2. The DNA of claim 1, wherein said polypeptide has the amino acid sequence of from position 35 to position 510 of the amino acid sequence SEQ ID NO: 2.

3. The DNA of claim 1, wherein said polypeptide has the amino acid sequence of from position 1 to position 510 of the amino acid sequence SEQ ID NO: 2.

4. The DNA of claim 1, which has the sequence of from position 103 to position 1530 of the DNA sequence SEQ ID NO: 1.

5. The DNA of claim 1, which has the sequence of from position 1 to position 1530 of the DNA sequence SEQ ID NO: 1.

6. The DNA of claim 1, which has the sequence of from position −41 to position 1582 of the DNA sequence SEQ ID NO: 1.

7. A plasmid, comprising a sequence of DNA which encodes a polypeptide having an amino acid sequence selected from the group consisting of:
   (a) from position 35 to position 510 of the amino acid sequence of SEQ ID NO: 2; and
   (b) from position 1 to position 510 of the amino acid sequence of SEQ ID NO: 2.

8. The plasmid of claim 7, wherein said polypeptide has the amino acid sequence of from position 35 to position 510 of the amino acid sequence SEQ ID NO: 2.

9. The plasmid of claim 7, wherein said polypeptide has the amino acid sequence of from position 1 to position 510 of the amino acid sequence SEQ ID NO: 2.

10. The plasmid of claim 7, wherein said sequence of DNA has the sequence of from position 103 to position 1530 of the DNA sequence SEQ ID NO: 1.

11. The plasmid of claim 7, wherein said sequence of DNA has the sequence of from position 1 to position 1530 of the DNA sequence SEQ ID NO: 1.

12. The plasmid of claim 7, wherein said sequence of DNA has the sequence of from position −41 to position 1582 of the DNA sequence SEQ ID NO: 1.

13. A transformed cell, which comprises a plasmid comprising a sequence of DNA which encodes a polypeptide having an amino acid sequence selected from the group consisting of:
   (a) from position 35 to position 510 of the amino acid sequence of SEQ ID NO: 2; and
   (b) from position 1 to position 510 of the amino acid sequence of SEQ ID NO: 2.

14. The transformed cell of claim 13, wherein said polypeptide has the amino acid sequence of from position 35 to position 510 of the amino acid sequence SEQ ID NO: 2.

15. The transformed cell of claim 13, wherein said polypeptide has the amino acid sequence of from position 1 to position 510 of the amino acid sequence SEQ ID NO: 2.

16. The transformed cell of claim 13, wherein said sequence of DNA has the sequence of from position 103 to position 1530 of the DNA sequence SEQ ID NO: 1.

17. The transformed cell of claim 13, wherein said sequence of DNA has the sequence of from position 1 to position 1530 of the DNA sequence SEQ ID NO: 1.

18. The transformed cell of claim 13, wherein said sequence of DNA has the sequence of from position −41 to position 1582 of the DNA sequence SEQ ID NO: 1.

* * * * *

UNITED STATES PATENT AND TRADEMARK OFFICE
CERTIFICATE OF CORRECTION

PATENT NO. : 5,691,180
DATED : November 25, 1997
INVENTOR(S) : John B. LOWE et al It is certified that error appears in the above-identified patent and that said Letters Patent is hereby corrected as shown below:

Column 3, line 59, delete "Ash" and insert --Asn--.
Column 4, line 28, delete "shows" and insert --show--.
Column 7, line 31, after "sub-terminal", delete "B" and insert --β--.
Column 13, line 66, delete "tranfected" and insert --transfected--.
Column 17, line 15, after "45 minutes", insert a period --.--.
Column 17, line 22, after "48 hours", insert a period --.--

Signed and Sealed this

Fifteenth Day of September, 1998

*Attest:*

BRUCE LEHMAN

*Attesting Officer*     Commissioner of Patents and Trademarks